US006232099B1

(12) United States Patent
Chapman et al.

(10) Patent No.: US 6,232,099 B1
(45) Date of Patent: May 15, 2001

(54) METHOD OF PRODUCING A CHIMERIC PROTEIN

(75) Inventors: Sean Nicholas Chapman; Simon Peter Santa Cruz; Karl John Oparka; Thomas Michael Aubrey Wilson, all of Dundee (GB)

(73) Assignee: Scottish Crop Research Institute (GB)

( * ) Notice: Subject to any disclaimer, the term of this patent is extended or adjusted under 35 U.S.C. 154(b) by 0 days.

(21) Appl. No.: 08/844,045

(22) Filed: Apr. 18, 1997

Related U.S. Application Data

(63) Continuation-in-part of application No. PCT/GB95/02457, filed on Oct. 18, 1995.

(30) Foreign Application Priority Data

| Oct. 18, 1994 | (GB) | ................................................ 9420989 |
| Jun. 9, 1995 | (GB) | ................................................ 9511729 |

(51) Int. Cl.[7] ............................. C12Q 1/70; C12P 21/06; C12N 7/00; C12N 15/00
(52) U.S. Cl. ...................... 435/69.3; 435/69.1; 435/69.7; 435/68; 435/235.1; 435/239; 435/320.1; 435/948
(58) Field of Search .................................. 435/69.1, 69.7, 435/69.3, 68.1, 235.1, 239, 320.1, 948

(56) References Cited

U.S. PATENT DOCUMENTS

| 4,332,897 | 6/1982 | Nakano et al. ...................... 435/69.1 |
| 4,348,477 | 9/1982 | Nakano et al. ........................... 435/5 |
| 4,348,478 | 9/1982 | Nakano et al. ...................... 435/69.1 |
| 4,407,956 | 10/1983 | Howell .............................. 435/235.1 |
| 4,722,840 | 2/1988 | Valenzuela et al. ............... 435/235.1 |
| 4,810,491 | 3/1989 | Minor et al. ....................... 435/235.1 |
| 4,857,634 | 8/1989 | Minor et al. ....................... 435/235.1 |
| 5,316,931 | * 5/1994 | Donson .............................. 435/172.3 |
| 5,618,699 | 4/1997 | Hamamoto et al. ..................... 435/5 |

FOREIGN PATENT DOCUMENTS

| 0 067 553 A2 | 12/1982 | (EP) . |
| 0 153 154 A1 | 8/1985 | (EP) . |
| 174759 | 3/1986 | (EP) . |
| 0 221 044 A1 | 5/1987 | (EP) . |
| WO 83/02393 | 7/1983 | (WO) . |
| WO 87/06261 | 10/1987 | (WO) . |
| WO 89/08145 | 9/1989 | (WO) . |
| WO 90/00611 | 1/1990 | (WO) . |
| 90/02184 | 3/1990 | (WO) . |
| 91/13542 | 9/1991 | (WO) . |
| 91/15587 | 10/1991 | (WO) . |
| 92/18618 | 10/1992 | (WO) . |
| 93/03161 | 2/1993 | (WO) . |
| 93/25068 | 12/1993 | (WO) . |
| 94/10329 | 5/1994 | (WO) . |
| WO 95/10624 | 4/1995 | (WO) . |
| WO 95/21248 | 8/1995 | (WO) . |
| WO 96/05292 | 2/1996 | (WO) . |

OTHER PUBLICATIONS

Jagadish et al., High Level Production of Hybrid Potyvirus–like Particles Carrying Repetitive Copies of Foreign Antigens in *Escherichia coli,* Bio/technology, vol. 11, Oct. 1993, pp 1166–1170.

Usha et al., Expression of an Animal Virus Antigenic Site on the Surface of a Plant Virus Particle, Virology, vol. 197, No. 1, Nov. 1993, pp 366–375.

Fitchen et al., Plant virus expressing hybrid coat protein with added murine epitope elicits autoantibody response, Vaccine 1995, vol. 13, No. 12, pp 1051–1057.

Haynes et al., Development of a Genetically–Engineered, Candidate Polio Vaccine Employing the Self–Assembling Properties of the Tobacco Mosaic . . . , Bio/technology, vol. 4, Jul. 1986, pp 637–641.

Hwang et al., Expression of tobacco mosaic virus coat protein and assembly of pseudovirus particles in *Escherichia coli,* Proc.Natl.Acad.Sci.USA, vol. 91, Sep. 1994, pp 9067–9071.

Takamatsu et al., Production of enkephalin in tobacco protoplasts . . . , FEBS Letters 08729, vol. 269, No. 1, Aug. 1990, pp 73–76.

Sugiyama et al., Systemic production of foreign peptides on the particle surface of tobacco mosaic virus, FEBS Letters 359 (1995) pp 247–250.

Hamamoto et al., A New Tobacco Mosaic Virus Vector and its use for the Systemic Production of Angiotensin–I–Converting Enzyme Inhibitor . . . , Bio/technology, vol. 11, Aug. 1993, pp 930–932.

Chapman et al., Potato virus X as a vector for gene expression in plants, The Plant Journal (1992) 2(4), pp 549–557.

Kavanagh et al., Molecular Analysis of a Resistance–Breaking Strain of Potato Virus X, Virology 189, 1992, pp 609–617.

Tetsuichiro Saito et al., "Mutational Analysis of the Coat Protein Gene of Tobacco Mosaic Virus in Relation to Hypersensitive Response in Tobacco Plants with the $N^1$ Gene," Virology 173, pp. 11–20, 1989.

Thomas H. Turpen et al., "Malarial Epitopes Expressed on the Surface of Recombinant Tobacco Mosaic Virus," Bio/Technology vol. 13, pp. 53–57, Jan. 13, 1995.

Roy French et al., "Bacterial Gene Inserted in an Engineered RNA Virus: Efficient Expression in Monocotyledonous Plant Cells," Science, vol. 231, pp. 1294–1297, Mar. 14, 1986.

(List continued on next page.)

Primary Examiner—Marianne P. Allen
Assistant Examiner—Mary K. Zeman
(74) Attorney, Agent, or Firm—Ratner & Prestia

(57) ABSTRACT

A method of producing a chimeric protein from ie a plant virus coding for such a protein. The method allows the production of large (ie 25 kDa) proteins which assemble with the virus in infected host cells and are arranged on the outer surface of chimeric viruses. A vector for the production of biologically useful proteins in such a manner is also disclosed.

49 Claims, 11 Drawing Sheets

OTHER PUBLICATIONS

Raul Andino et al., "Engineering Poliovirus as a Vaccine Vector for the Expression of Diverse Antigens," Science, vol. 265, pp. 1448–1451, Sep. 2, 1994.

D.D. Shukla et al., "The N and C Termini of the Coat Proteins of Potyviruses Are Surface–located and the N Terminus Contains the Major Virus–specific Epitopes," Journal of General Virology, vol. 69, pp. 1497–1508, 1988.

Jeremy D. A. Kitson et al., "Chimeric Polioviruses That Include Sequences Derived from Two Independent Antigenic Sites of Foot–and–Mouth Disease Virus (FMDV) Induce Neutralizing Antibodies against FMDV In Guinea Pigs," Journal of Virology, vol. 65, No.6, pp. 3068–3075, Jun. 1991.

Karen L. Burke et al., "A Cassette Vector for the Construction of Antigen Chimaeras of Poliovirus," Journal Of General Virology, vol. 70, pp. 2475–2479, 1989.

M. James C. Crabbe et al., "Modelling of poliovirus HIV–1 antigen chimaeras," FEBS, vol. 271, No. 1, 2, pp. 194–198, Oct. 1990.

Annette Martin et al., "Engineering a poliovirus type 2 antigenic site on a type 1 capsid results in a chimaeric virus which is neurovirulent for mice," The EMBO Journal, vol. 7, No. 9, pp. 2839–2847, 1988.

J.M. Hogle et al., "Three–Dimensional Structure of Poliovirus at 2.9 Å Resolution," Science vol. 229, pp. 1358–1365, Sep. 27, 1985.

David J. Evans et al., "An engineered poliovirus chimaera elicits broadly reactive HIV–1 neutralizing antibodies," Letters to Nature, vol. 339, pp. 385–388, Jun. 1, 1989.

Karen L. Burke et al., "Antigen chimaeras of poliovirus as potential new vaccines", Letters to Nature, vol. 332, pp. 81–82, Mar. 3, 1988.

Johannes T. Dessens et al., "Mutational Analysis ofthe Putative Catalytic Triad of the Cowpea Mosaic Virus 24K Protease," Virology, vol. 184, pp. 738–746, 1991.

Owen Jenkins et al., "An Antigen Chimera of Poliovirus Induces Antibodies against Human Papillomavirus Type 16," Journal of Virology, vol. 64, No. 3, pp. 1201–1206, Mar. 1990.

Paul Ahlquist et al., "Nucleotide Sequence of the Brome Mosaic Virus Genome and its Implications for Replication," J. Molecular Biology, vol. 172, pp. 369–383, 1984.

A.D. Murdin et al., "Phenotypic characterization of antigenic hybrids of poliovirus," Microbial Pathogenesis, vol. 10, pp. 39–45, 1991.

A.D. Murdin et al., "The effect of site and mode of expression of a heterologous antigenic determinant on the properties of poliovirus hybrids," Microbial Pathogenesis, vol. 10, pp. 27–37, 1991.

Zhongguo Chen et al., "Capsid structure and RNA packaging in comoviruses," seminars in Virology, vol. 1, pp. 453–466, 1990.

Michael M. Sveda et al., "Functional expression in primate cells of cloned DNA coding for the hemagglutinin surface glycoprotein of influenza virus," Proc. Nat'l. Acad. Sci., vol. 78, No. 9, pp. 5448–5492, Sep. 1981.

Hugh S. Mason et al., "Expression of hepatitis B surface antigen in transgenic plants," Proc. Natl'l. Acad. Sci., vol. 89, pp. 11745–11749, Dec. 1992.

Jonathan B. Rohll et al., "3–Terminal Nucleotide Sequences Important for the Accumulation of Cowpea Mosaic Virus M–RNA," Virology, vol. 193, pp. 672–679, 1993.

Douglas R. Black et al., "Structure and Infectivity of Picornaviral RNA Encapsidated by Cowpea Chlorotic Mottle Virus Protein," Journal of Virology, vol. 12, No. 6, pp. 1209–1215, Dec. 1973.

D.E. Sleat et al., "Packaging of Recombinant RNA Molecules into Pseudovirus Particles Directed by the Origin–of–Assembly Sequence from Tobacco Mosaic Virus RNA," Virology, vol. 155, pp. 299–308, 1986.

Robert Sacher et al., "Hybrid Brome Mosaic Virus RNAs Express and Are Packaged in Tobacco Mosaic Virus Coat Protein in Vivo," Virology, vol. 167, pp. 15–24, 1988.

C.L. Holness et al., "Identification of the Initiation Codons for Translation of Cowpea Mosaic Virus Middle Competent RNA Using Site–Directed Mutagenesis of an Infectious cDNA Clone," Virology 172, pp. 311–320, 1989.

G.P. Lomonossoff et al., "The Synthesis and Structure of Comovirus Capsids," Prog. Biophys. Molec. Biol. vol. 55, pp. 107–137, 1991.

Zhongguo Chen et al., "Protein–RNA Interaction in an Icosahedral Virus at 3.0 Å Resolution," Science, vol. 245, pp. 154–159, 1989.

Bruno Zaccomer et al., "The remarkable variety of plant RNA virus genomes," Journal of General Virology, vol. 76, pp. 231–247, 1995.

Thorleif Joelson et al., "Presentation of a foreign peptide on the surface of tomato bushy stunt virus," Journal Of General Virology, vol. 78, pp. 1213–1217, 1997.

Kristian Dalsgaard et al., "Plant–derived vaccine protects target animals against a viral disease," Nature Biotechnology, vol. 15, pp. 248–252, Mar. 1997.

George P. Lomonossoff, "Plant viruses and pharmaceuticals," Agro–Food–Industry–Hi–Tech, pp. 7–11, Mar./Apr. 1995.

Tianwei Lin et al., "Structure–based design of peptide presentation on a viral surface: the crystal structure of a plant/animal virus chimera at 2.8 Å resolution," Folding & Design, vol. 1, No. 3, pp. 179–187, Apr. 17, 1996.

George Lomonossoff et al., "Eukaryotic viral expression systems for polypeptides," seminars in Virology, vol. 6, pp. 257–267, 1995.

Rob Goldbach et al., "Evolution of Plus–Strand RNA Viruses," Intervirology, vol. 29, pp. 260–267, 1988.

Rob Goldbach et al., "Genetic Organization, Evolution and Expression of Plant Viral RNA Genomes," Proceedings of the NATO Advanced Research Workshop on Recognition and Response in Plant–Virus Interactions, held at Chichester, West Sussex, UK, Apr. 12–16, 1989, 10 pp.

J. Johnson et al., "Presentation of Heterologous Peptides on Plant Viruses: Genetics, Structure, and Function," Annu. Rev. Phytopathol., vol. 35, pp. 67–86, 1997.

Ryan et al. 1994 The EMBO Journal vol. 13 No. 4 (Feb. 15) p 928–933, Feb. 1994.*

* cited by examiner

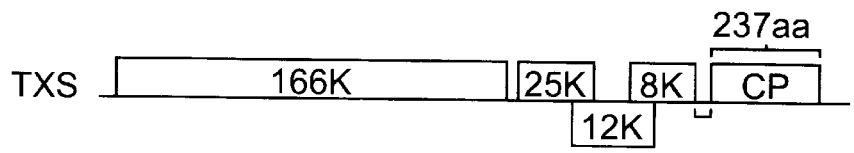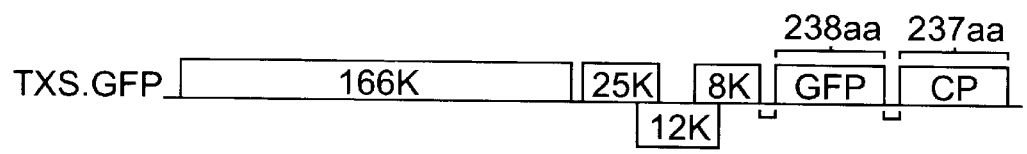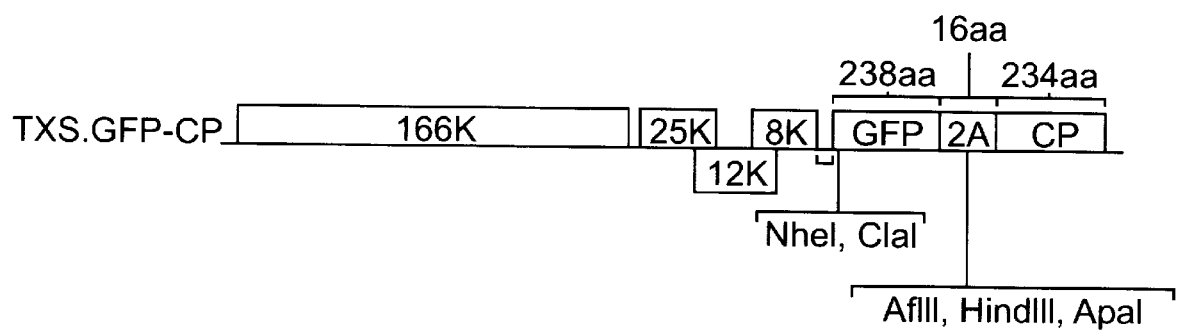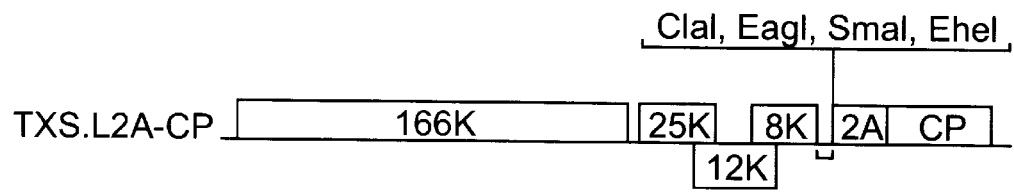
Fig. 1a

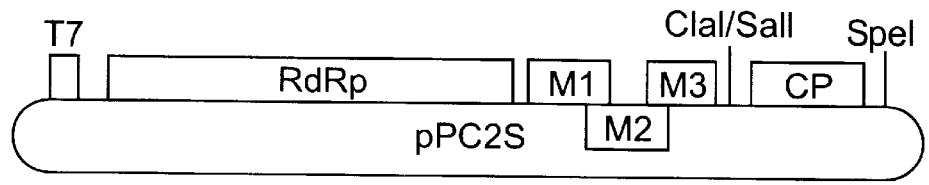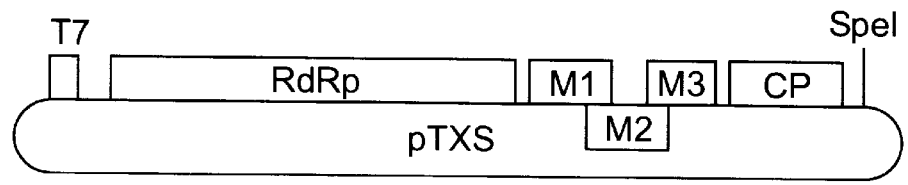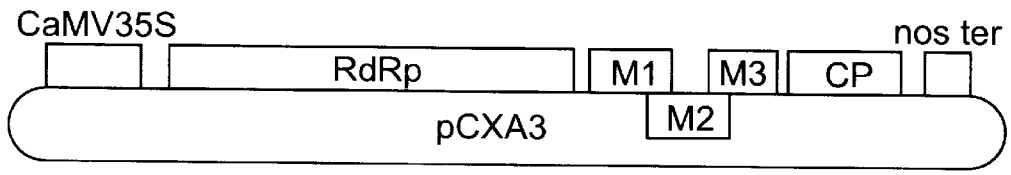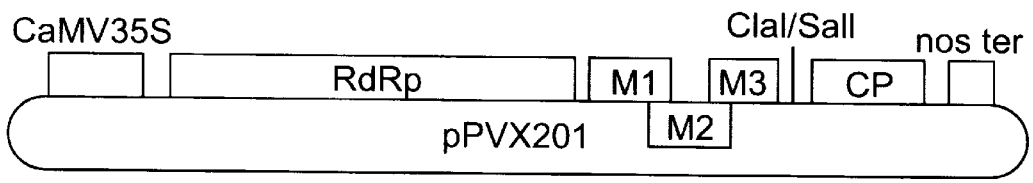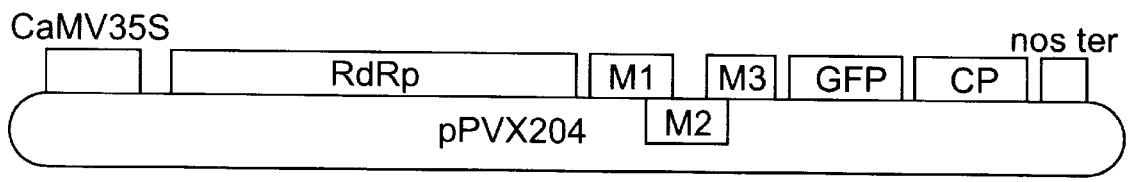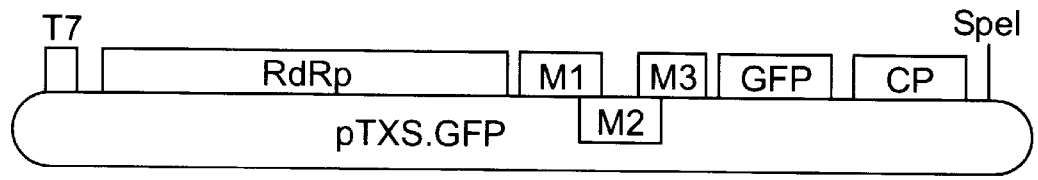
Fig. 1b

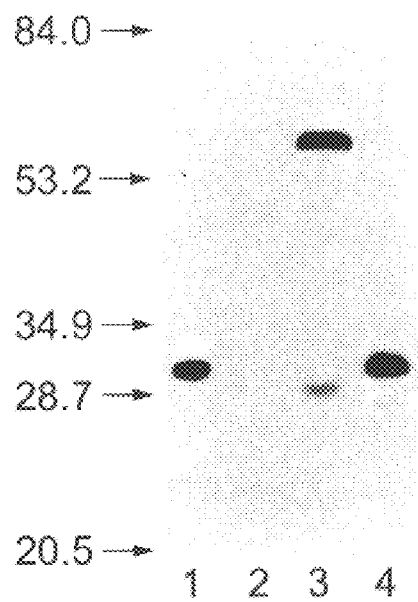
Fig. 2
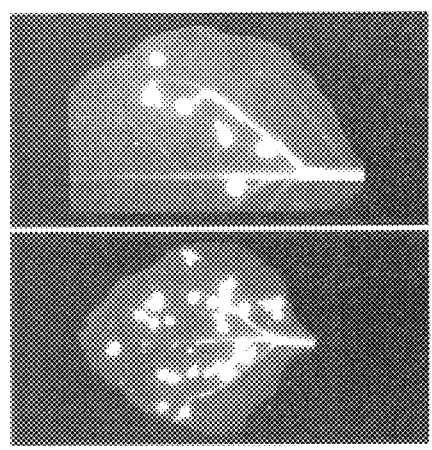
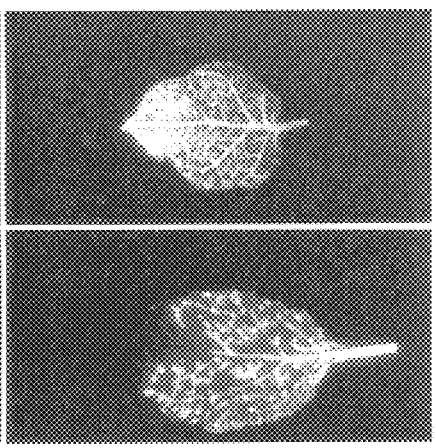
Fig. 3A    Fig. 3B
Fig. 3c    Fig. 3d pLit.GFP-2A₂₃H-CP

```
TCC GGA TCT AGA GCA CCT GTG AAA CAG CTG TTG AAT TTT GAC CTT CTT AAG CTT GCG GGA GAC GTC GAG TCC AAC CCT GGG
 S   G   S   R   A   P   V   K   Q   L   L   N   F   D   L   L   K   L   A   G   D   V   E   S   N   P   G.
``` pLit.GFP-2A₁₆H-CP

```
                        TCC GGA TCT AGA AAT TTT GAC CTT CTT AAG CTT GCG GGA GAC GTC GAG TCC AAC CCT GGG
                         S   G   S   R   N   F   D   L   L   K   L   A   G   D   V   E   S   N   P   G.
``` pLit.GFP-2A₁₆K-CP

```
                        TCC GGA TCT AGA AAT TTT GAC CTT CTC AAG TTG GCG GGA GAC GTC GAG TCC AAC CCT GGG
                         S   G   S   R   N   F   D   L   L   K   L   A   G   D   V   E   S   N   P   G.
``` pLit.GFP-2A₅₈K-CP

```
TCC GGA TCT AGA GTC ACC GAG TTG CTT TAC CGG ATG AAG AGG GCC GAA ACA TAC TGT CCA AGG CCC TTG CTG GCA ATC CAC CCA ACT GAA GCC
 S   G   S   R   V   T   E   L   L   Y   R   M   K   R   A   E   T   Y   C   P   R   P   L   L   A   I   H   P   T   E   A.
AGA CAC AAA CAG AAA ATT GTG GCA CCG AAA CAG ACT TTG AAT TTT GAC CTT CTC AAG TTG GCG GGA GAC GTC GAG TCC AAC CCT GGG
 R   H   K   Q   K   I   V   A   P   K   Q   T   L   N   F   D   L   L   K   L   A   G   D   V   E   S   N   P   G.
```

Fig. 8

66—
45— 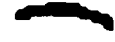
31—
21.5—
14.5—
*Fig. 11A*
66—
45— 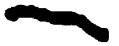
31—
21.5—
14.5—
*Fig. 11B*

SEQUENCE LISTING

```
<160> NUMBER OF SEQ ID NOS: 19

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:portion of
      the plasmid pTXS at the junction between Potato Virus
      X sequence and Promoter T7 sequence
<221> NAME/KEY: misc_feature
<222> LOCATION: (1)..(13)
<223> OTHER INFORMATION: 5' transcribed portion in the viral genome of
      the potato virus X sequence in plasmid pTXS
<221> NAME/KEY: misc_feature
<222> LOCATION: (14)..(26)
<223> OTHER INFORMATION: 3' non-transcribed portion of the promoter T7
      sequence plasmid pTXS

<400> SEQUENCE: 1
gatttggaga ggagaaaact aaacca                                          26

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer
      directed to the Green Fluorescent Protein  of
      Aequorea Victoria gene
<221> NAME/KEY: misc_feature
<222> LOCATION: (12)..(14)
<223> OTHER INFORMATION: initiation codon of the Green Fluorescent
      Protein (GFP)

<400> SEQUENCE: 2
```

```
gccaatcgat catgagtaaa ggag                                           24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer
      directed to the gene of the Green Fluorescent
      Protein of Aequorea victoria
<221> NAME/KEY: misc_feature
<222> LOCATION: (15)..(17)
<223> OTHER INFORMATION: termination codon of the Green Fluorescent
      Protein gene

<400> SEQUENCE: 3
ggaagtcgac acatttattt g                                              21

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide used as primer

<400> SEQUENCE: 4
tcggccgtcc cggggcg                                                   18

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide used as primer

<400> SEQUENCE: 5
aaagcttaag aaggtcaaaa ttggcgcccc cgggacggcc ga                       42

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: nucleotide
      sequence linker
<221> NAME/KEY: CDS
<222> LOCATION: (15)..(32)

<400> SEQUENCE: 6
atcgatccgg ccgt ccc ggg ggc gcc aat ttt                              32
               Pro Gly Gly Ala Asn Phe
                 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: translation
      of the polylinker  of vector pTXS.L2a-CP

<400> SEQUENCE: 7

Pro Gly Gly Ala Asn Phe
  1               5

<210> SEQ ID NO 8
```

```
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide used as primer

<400> SEQUENCE: 8
caatgggccc tatacaatca actct                                          25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide used as primer

<400> SEQUENCE: 9
agcggataac aatttcacac agga                                           24

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide used as primer

<400> SEQUENCE: 10
tcaatcgtcg acatgagtaa aggagaagaa                                     30

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide used as primer

<400> SEQUENCE: 11
tgtactaaag aaatccccat cc                                             22

<210> SEQ ID NO 12
<211> LENGTH: 81
<212> TYPE: DNA
<213> ORGANISM: Foot-and-mouth disease virus
<220> FEATURE:
<221> NAME/KEY: CDS
<222> LOCATION: (1)..(81)

<400> SEQUENCE: 12 tcc gga tct aga gca cct gtg aaa cag ctg ttg aat ttt gac ctt ctt      48
Ser Gly Ser Arg Ala Pro Val Lys Gln Leu Leu Asn Phe Asp Leu Leu
 1               5                  10                  15 aag ctt gcg gga gac gtc gag tcc aac cct ggg                          81
Lys Leu Ala Gly Asp Val Glu Ser Asn Pro Gly
             20                  25

<210> SEQ ID NO 13
<211> LENGTH: 27
<212> TYPE: PRT
<213> ORGANISM: Foot-and-mouth disease virus

<400> SEQUENCE: 13

Ser Gly Ser Arg Ala Pro Val Lys Gln Leu Leu Asn Phe Asp Leu Leu
 1               5                  10                  15
```

Lys Leu Ala Gly Asp Val Glu Ser Asn Pro Gly
            20                  25

<210> SEQ ID NO 14
<211> LENGTH: 60
<212> TYPE: DNA
<213> ORGANISM: Foot-and-mouth disease virus
<220> FEATURE:
<221> NAME/KEY: CDS
<222> LOCATION: (1)..(60)

<400> SEQUENCE: 14 tcc gga tct aga aat ttt gac ctt ctt aag ctt gcg gga gac gtc gag      48
Ser Gly Ser Arg Asn Phe Asp Leu Leu Lys Leu Ala Gly Asp Val Glu
 1               5                  10                  15 tcc aac cct ggg                                                      60
Ser Asn Pro Gly
            20

<210> SEQ ID NO 15
<211> LENGTH: 20
<212> TYPE: PRT
<213> ORGANISM: Foot-and-mouth disease virus

<400> SEQUENCE: 15

Ser Gly Ser Arg Asn Phe Asp Leu Leu Lys Leu Ala Gly Asp Val Glu
 1               5                  10                  15

Ser Asn Pro Gly
            20

<210> SEQ ID NO 16
<211> LENGTH: 60
<212> TYPE: DNA
<213> ORGANISM: Foot-and-mouth disease virus
<220> FEATURE:
<223> OTHER INFORMATION: Description of Unknown Organism:NIL
<221> NAME/KEY: CDS
<222> LOCATION: (1)..(60)

<400> SEQUENCE: 16 tcc gga tct aga aat ttt gac ctt ctc aag ttg gcg gga gac gtc gag      48
Ser Gly Ser Arg Asn Phe Asp Leu Leu Lys Leu Ala Gly Asp Val Glu
 1               5                  10                  15 tcc aac cct ggg                                                      60
Ser Asn Pro Gly
            20

<210> SEQ ID NO 17
<211> LENGTH: 20
<212> TYPE: PRT
<213> ORGANISM: Foot-and-mouth disease virus

<400> SEQUENCE: 17

Ser Gly Ser Arg Asn Phe Asp Leu Leu Lys Leu Ala Gly Asp Val Glu
 1               5                  10                  15

Ser Asn Pro Gly
            20

<210> SEQ ID NO 18
<211> LENGTH: 183
<212> TYPE: DNA
<213> ORGANISM: Foot-and-mouth disease virus
<220> FEATURE:
<221> NAME/KEY: CDS
<222> LOCATION: (1)..(183)

```
<400> SEQUENCE: 18 tcc gga tct aga gtc acc gag ttg ctt tac cgg atg aag agg gcc gaa       48
Ser Gly Ser Arg Val Thr Glu Leu Leu Tyr Arg Met Lys Arg Ala Glu
 1               5                  10                  15 aca tac tgt cca agg ccc ttg ctg gca atc cac cca act gaa gcc aga       96
Thr Tyr Cys Pro Arg Pro Leu Leu Ala Ile His Pro Thr Glu Ala Arg
             20                  25                  30 cac aaa cag aaa att gtg gca ccg gtg aaa cag act ttg aat ttt gac      144
His Lys Gln Lys Ile Val Ala Pro Val Lys Gln Thr Leu Asn Phe Asp
         35                  40                  45 ctt ctc aag ttg gcg gga gac gtc gag tcc aac cct ggg                  183
Leu Leu Lys Leu Ala Gly Asp Val Glu Ser Asn Pro Gly
     50                  55                  60

<210> SEQ ID NO 19
<211> LENGTH: 61
<212> TYPE: PRT
<213> ORGANISM: Foot-and-mouth disease virus

<400> SEQUENCE: 19

Ser Gly Ser Arg Val Thr Glu Leu Leu Tyr Arg Met Lys Arg Ala Glu
 1               5                  10                  15

Thr Tyr Cys Pro Arg Pro Leu Leu Ala Ile His Pro Thr Glu Ala Arg
             20                  25                  30

His Lys Gln Lys Ile Val Ala Pro Val Lys Gln Thr Leu Asn Phe Asp
         35                  40                  45

Leu Leu Lys Leu Ala Gly Asp Val Glu Ser Asn Pro Gly
     50                  55                  60
```

METHOD OF PRODUCING A CHIMERIC PROTEIN

This is a continuation in part of International Application No. PCT/GB95/02457, Oct. 18, 1995.

This invention relates to a method of producing a chimeric protein, eg a biologically active protein such as an antibiotic peptide.

Typical antibiotic peptides include the marginins, 23 amino acid-long alpha-helical peptides, originally identified from frog skin, which have a significant antibacterial activity; the defensins which combat bacteria, fungi and some enveloped viruses such as herpes simplex virus and HIV; and the protegrins which are 16–18 amino acid-long antibiotic peptides with strong biocidal activity.

The protegrins form part of an array of antibiotic peptides that are used by mammalian phagocytes to destroy invading pathogens through non-oxidative processes. Typically the protegrins include 4 cysteine residues and form a double-stranded β-sheet structure and show sequence similarity with the antibiotic defensin peptides that are also involved in phagocyte defence responses. The defensins are cationic, cysteine-rich peptides of 29 to 34 amino acids that are formed almost entirely of β-sheet structures and that have been shown to have biocidal activity against bacteria, fungi and some enveloped viruses, including herpes simple virus and HIV. Both the protegrins and defensins are expressed in phagocytes as pre-pro-proteins which are cleaved to release the biocidal peptides from the carboxy-terminus of the protein.

Because of their antibacterial activity it may not be convenient to synthesize these antibiotic peptides by genetic engineering in conventional prokaryotic expression systems. Solution synthesis of large amounts of these peptides with a variety of amino acid modifications may be possible, but is not currently considered commercially viable, since a significant drop in yield occurs in the manufacture of peptides of over 25–30 amino acid residues.

Eukaryotic expression systems (yeast, insect, animal or plant cells which produce foreign proteins or peptides) may be necessary if there is a need for post-transitional modification of the desired protein, but fermentation processes for such eukaryotic expression systems are expensive to maintain, provide little flexibility in terms of scaling the process up to industrial production levels and are very susceptible to contamination. Processing and purification of the desired protein can also be complex and costly.

The use of plants and benign plant viruses offers an opportunity to produce foreign proteins with minimal host cell contamination, thereby reducing contamination problems which could affect successful achievement of the required regulatory body approval for human or veterinary applications.

It has been proposed in WO92/18618 to use plant viruses as vector systems for the expression of foreign nucleotide sequences. WO92/18618 describes the use of a Comovirus (Cowpea Mosaic Virus or CPMV) as an effective vector for such expression and also mentions other spheroidal viruses such as HIV and Picorna-viruses. Picornaviridae generally comprise particles of 22–30 nm having cubic symmetry; Comoviridae have a pair of 28 nm particles with a similar symmetry, and HIV is a member of the Retroviridae which are generally enveloped 100 nm particles containing an icosahedral nucleocapsid.

One disadvantage of the system disclosed in WO92/18618 is that the geometry of the spheroidal viruses precludes large proteins from being produced, since the size and number of chimeric proteins per virus particle (generally 60 for icosahedral virus particles) is limited by the spheroidal geometry of the virus.

Construction of chimeric proteins in such viruses is also limited to the insertion of the foreign component into a loop in a native virus protein, eg the β-B to β-C loop in VP23 of CPMV, where such insertion does not affect the geometry of the coat protein and/or its ability to self-assemble into a virus particle (virion). As can be appreciated, the size of the peptide which can be tolerated in such an insertion is fairly limited; polypeptides of a maximum of 26 amino acids in length are cited by WO92/18618. Larger polypeptides present in internal insertion sites in coat or capsid proteins of the viruses exemplified may result in disruption of the geometry of the protein and/or its ability to successfully interact with other coat proteins leading to failure of the chimeric virus to assemble. Modified viruses which cannot self-assemble might not infect other host cells and produce whole plant infection. This possible lack of ability to spread the infection of the modified virus constitutes a significant disadvantage in the prior system.

The present invention contemplates the use of benign high copy number rod-shaped viruses, preferably plant viruses such as potato virus X (PVX), to produce foreign protein connected to viral coat protein subunits. When assembled, the virus particles comprise long helical arrays of more than 1000 identical chimeric proteins (which are typically coat protein—foreign protein fusion molecules) per virion. Generally the foreign protein portion will be displayed on the outer surface of the virus particles.

A suitable proteolytic degradation site (eg elastase or CNBr) may be engineered into the chimeric protein to permit release of the foreign protein portion from purified virus material. Given the size of the foreign protein and the relevant composition of the possible viruses, it is estimated that between 10 and 30% of the total weight yield of virus particle could comprise the foreign protein. Release of the foreign protein by proteolytic cleavage can be a simple purification regime, followed by removal of the residual innocuous plant virus itself. Yields of plant virus up to 5 g per kg wet weight of leaf from potato or tobacco are possible and hence the yields of foreign protein could be very substantial.

If the foreign protein is left attached to the chimeric protein in the virus particle, the whole virus particle can also be used as a vector for expression and presentation of peptide epitopes for vaccination of animals and/or the delivery of therapeutic single-stranded RNA molecules. This may be utility in the delivery of anti-sense or triplex nucleotides.

The present invention provides a method of producing a chimeric protein comprising:

a. providing a rod-shaped recombinant virus or pseudovirus containing a polynucleotide encoding a chimeric protein having a first (viral) portion and a second (non-viral) portion, the chimeric protein being capable of assembly into a virus particle such that the second portion is disposed on the exterior surface of the assembled virus particle;

b. infecting a host cell with the virus or pseudovirus; and c. allowing replication of the virus or pseudovirus and expression of the chimeric protein in the host cell.

The term "rod-shaped" as applied herein to viruses includes filamentous or flexuous viruses, which are preferred. It is advantageous to use a virus which is flexuous (ie which can bend easily) since chimeric proteins with large second portions may be able to assemble more easily into virus particles (virions) which are flexuous than those which are rigid. PVX is preferred since it forms a flexuous virion.

The virus or pseudovirus can preferably assemble in the host cell to produce infective virus particles which comprise nucleic acid and chimeric protein. This enables the infection of adjacent cells by the infective virus or pseudovirus particle and expression of the chimeric protein therein.

The host cell can be infected initially with virus or pseudovirus in particle form (ie in assembled rods comprising nucleic acid and protein) or alternatively in nucleic acid form (ie RNA such as viral RNA; cDNA or run-off transcripts prepared from cDNA) provided that the virus nucleic acid used for initial infection can replicate and cause production of whole virus particles having the chimeric protein.

The term "pseudovirus" as used herein means a virus-derived nucleic acid sequence optionally assembled into particles and having an incomplete viral genome as compared to wild-type virus but retaining sufficient viral genes to allow replication and assembly of the pseudovirus. The virus or pseudovirus may contain genetic material foreign to the wild-type virus.

Optionally, the virus or pseudovirus can be purified from the host cell in order to concentrate the chimeric protein, ie by polyethylene glycol precipitation and/or density gradient centrifugation.

Optionally, the method may include the step of separating a protein derived from the second portion from the remainder of the chimeric protein after the virus or pseudovirus has been purified from the host cell.

A linker peptide can be incorporated between the first and second portions and may have the function of spacing the two portions from one another, reducing stearic restrictions. Optionally the linker peptide may contain a proteolytic or chemical cleavage site.

The term "proteolytic or chemical cleavage site" refers to a short sequence of amino acids which is recognisable and subsequently cleavable by a proteolytic enzyme or chemical means. Suitable proteolytic enzymes include trypsin, pepsin, elastase and the like. Alternatively the proteolytic or chemical cleavage site may be a site which is vulnerable to cleavage by other means, for example by addition of chemicals such as cyanogen bromide (CNBr) or acids or by shear. Preferably, the proteolytic or chemical cleavage site is an elastase cleavage site, but other suitable proteolytic cleavage sites can be used with corresponding enzymes.

The protein derived from the second portion may be separated from the remainder of the chimeric protein before assembly of the virus particle, eg during expression of the genetic material coding for the chimeric protein, or during assembly of the chimeric protein into a virus particle. In this embodiment the host cell will contain free protein derived from the second portion. This embodiment can be useful when expression of very large proteins derived from the second portion is desired. In such an embodiment, the proteolytic or chemical cleavage site may be selected to cleave automatically in a virally-infected host cell.

The term "proteolytic or chemical cleavage site" may thus also include sequences that cleave automatically such as the FMDV (Foot and Mouth Disease Virus) 2A protease.

The proteolytic or chemical cleavage site may be an integral part of either the first or second portion. Hence either/or both of the portions may include an integral proteolytic or chemical cleavage site.

Thus the present invention also provides a method of producing a chimeric protein as defined above, wherein the protein derived from the second portion is purified directly from the host cell after expression.

The second portion and/or the protein derived therefrom may be relatively large eg over 10 kDa. Proteins of 25–30 kDa are suitable for production by the method and even proteins up to 60–70 kDa have been shown to be produced by the method of the invention.

The first (viral) portion of the chimeric protein may be any protein, polypeptide or parts thereof, derived from a viral source including any genetically modified versions thereof (such as deletions, insertions, amino acid replacements and the like). In certain embodiments the first portion will be derived from a viral coat protein (or a genetically modified version thereof). Mention may be made of the coat protein of Potato Virus X as being suitable for this purpose. Preferably the first portion has the ability to aggregate into particles by first-portion/first portion association. Thus, a chimeric protein molecule can assemble with other chimeric protein molecules or with wild-type coat protein into a chimeric virion.

In a preferred embodiment of the invention the particle is derived from a potyvirus or even more preferably a potexvirus such as PVX, and in such an embodiment, the second portion is preferably disposed at or adjacent the N-terminus of the coat protein. In PVX, the N-terminus of the coat protein is believed to form a domain on the outside of the virion.

The second portion of the chimeric protein may be any protein, polypeptide of parts thereof, including any genetically modified versions thereof (such as deletions, insertions, amino acid replacements and the like) derived from a source other than the virus from which the first portion is derived. In certain embodiments the second portion or the protein derived therefrom is a biologically active or useful molecule. The second portion or the protein derived therefrom may also be a diagnostic reagent, an antibiotic or a therapeutic or pharmaceutically active agent. Alternatively the second portion or the protein derived therefrom may be a food supplement.

In an alternative embodiment, the second portion or the protein derived therefrom may be an indicator protein chosen for its ability to indicate the location of the chimeric protein or of the virus particle. Such an example is the 25 kDa jellyfish green fluorescent protein.

The polynucleotide coding for the second (non-viral) portion may be inserted into an appropriate restriction site in the viral genome. The restriction site adopted for such insertion may be naturally occurring in the viral genome or artificially constructed therein and the polynucleotide coding for the second portion may be ligated therein by conventional means. General techniques for cloning of foreign nucleic acid and construction of chosen restriction sites is comprehensively described in the art and is within the scope of the skilled person.

It is preferred that the polynucleotide coding for the second portion is inserted at or adjacent a terminus of the polynucleotide coding for the first portion, such that upon translation the chimeric protein has the first portion at one end and the second portion at the opposite end. It is not necessary for the first portion to comprise a whole virus cost protein, but this remains an option.

The virus particle may be formed by the assembly of chimeric proteins only or by the mixed assembly of chimeric proteins together with some unmodified or less modified forms of the naturally occurring wild-type coat protein which forms the basis of the first portion. For a mixed virus particle of the latter type, there must be present polynucleotide(s) encoding the chimeric protein and the naturally occurring coat protein. The appropriate protein-coding sequences may be arranged in tandem on the same molecule. An alternative would be co-infection (for example of mutually dependent defective viruses or pseudoviruses) of two or more viruses or pseudoviruses, or infection by chimeric virus of a host cell or whole organism (such as a plant) which expresses such a protein intrinsically.

An advantage is gained by using a virus which forms a particle with a relatively high pitch of helix. PVX has a pitch of 3.4 nm and is to be preferred over viruses with a lower pitch. Virus particles with higher pitches may be able to accommodate larger protein insertions on their surfaces since their coat proteins assemble with more space between them than coat proteins of viruses with lower pitches.

A virus or pseudovirus genetically modified to express the chimeric protein forms a further aspect of the present invention, as does any host cell infected with such a virus or pseudovirus.

Preferably, the host cell used to replicate the virus or pseudovirus is a plant cell where the virus is a plant virus, although insect cells, mammalian cells and bacteria can be used with viruses which will replicate in such cells.

The present invention also provides a virus-like particle comprising nucleic acid and protein, the protein having a first (viral) portion and a second (non-viral) portion.

The term "virus-like particle" refers to self-assembling particles which have a similar physical appearance to virus particles and includes pseudoviruses. Virus-like particles may lack or possess dysfunctional copies of certain genes of the wild-type virus, and this may result in the virus-like-particle being incapable of some function which is characteristic of the wild-type virus, such as replication and/or cell-cell movement.

The nucleic acid can be DNA or RNA, according to the genome of the virus from which the virus-like particle is derived. The nucleic acid may comprise an origin-of-assembly sequence (OAS) by which we mean a nucleic acid sequence which permits initiation of assembly of the protein and nucleic acid into virus-like particles.

Further according to the invention there is provided a method of producing a protein having a first (viral) portion and a second (non-viral) portion, the method comprising expressing the protein in a cell, providing a nucleic acid sequence capable of assembly with the protein into a virus-like particle (VLP), and permitting in vivo assembly of the protein and nucleic acid into VLPs.

The virus-like particles can be purified from the cell by standard techniques such as centrifugation etc, and the chimeric protein can optionally be cleaved to release the second portion from the first portion, or separated entirely from the nucleic acid. If the chimeric protein is left attached to the virus-like particle, the whole virus-like particle can also be used for presentation of peptide epitopes for vaccination of animals, the production of therapeutic or industrial proteins and polypeptides and/or the delivery of therapeutic nucleic acid molecules (optionally targeted delivery), such as ss or ds DNA or RNA, including antisense molecules.

The nucleic acid can advantageously be provided from a plasmid in the cell, possibly by transcription of such a plasmid. The protein may be encoded by the same or another plasmid in the cell. Alternatively, one or both of the nucleic acid and protein can be coded from the genome of the cell.

The cell is preferably a bacterium such as *E. coli* although other forms of bacteria and other cells may be useful, such as mammalian cells, plant cells, yeast cells and insect cells. The cell may be a natural host cell for the virus from which the virus-like particle is derived, but this is not necessary.

The use of a cell for the assembly of the virus-like particle in vivo enables facile cell handling techniques to be employed to facilitate purification of virus-like particles and purification of protein. In addition, where it is desired to produce a second portion protein which is toxic to some cells (eg plant cells) a different (eg bacterial) cell may be employed.

The nucleic acid is preferably chosen in accordance with its ability to assemble with the viral protein. For example, the virus-like particle may be derived from tobacco mosaic virus (TMV). In such a case, the first portion of the protein is preferably derived from TMV coat protein (CP), and the nucleic acid has at least an OAS of eg 75 or more nucleotides derived from TMV RNA. The sequence of the remainder of the nucleic acid is not important, and it can be chosen to code for the chimeric protein or may be of some other eg unrelated or therapeutic sequence. The inclusion of nucleic acid in the virus-like particle means that the particle is of helical symmetry and more stable than simple aggregations of protein (eg planar, stacked or helical arrays), which are normally created at low pH in vitro from purified TMV coat protein, and can dissociate outside a narrow pH range. Also, the length of the particles can be selected by specifying a particular length of nucleic acid. This results in a more uniform range of particle sizes, which has advantages in purification procedures such as centrifugation, and in defining and regulating the quality control for products for medical use.

A further advantage with the use of nucleic acid in the assembly of virus-like particles is that the resultant particle can have a regular multivalent and true helical structure which can be more immunogenic than an aggregation of protein or free subunits of protein. The greater stability of the particle can also provide longer access to the immune system in certain embodiments.

The second portion of the chimeric protein is preferably disposed on the outer surface of the virus-like particle. Thus where the particle is derived from TMV, the second portion can be disposed on the amino or carboxy terminus, or inserted in eg an internal loop disposed on the outer surface of the CP. This can result in improved assembly as compared with the assembly of particles having a second portion on another location of the CP, and can enhance immune recognition of the second portion on the particle surface, which is useful for embodiments where the CP is an immunogen such as a vaccine. In certain cases it may be possible to provide large second portion proteins.

In a preferred embodiment of the invention the particle is derived from a tobamovirus such as tobacco mild green mosaic virus TMGMV), tobacco mosaic virus (TMV), or from a potexvirus such as PVK, and in such an embodiment, the second portion is preferably disposed at or adjacent the N-terminus of the coat protein. In PVX, the N-terminus of the coat protein is believed to form a domain on the outside of the virion.

The virus particle may be formed by the assembly of chimeric proteins only or by the mixed assembly of chimeric proteins together with some unmodified or less modified forms of the naturally occurring wild-type coat protein which forms the basis of the first portion. For a mixed virus particle of the latter type, there must be present polynucleotide(s) encoding the chimeric protein and the naturally occurring coat protein. The appropriate protein-coding sequence(s) may be arranged in tandem on the same molecule, or could be generated by differential RNA splicing. Alternatively, the different proteins could be translated from the same nucleotide sequence and modified later, eg by in vivo processing such as self cleavage. An example of this is the provision of a chimeric CP gene encoding eg GFP-2A-CP fusion protein, which is expressed from a single gene (eg on a plasmid, from the genome of the cell, or from the RNA of the VLP) and which self cleaves a variable number of the translated proteins into separate GFP and CP, a proportion of the translated proteins remaining uncleaved as GFP-2A-CP. Thus a heterologous mixture of CPs can be assembled into a VLP, with eg every 10th CP bearing a second portion, and the remaining CPs being cleaved, native (or substantially native) CPs. Thus the potential problems with stearic hindrance which might occur if all the CPs were chimeric can be overcome. Suitable co-translational cleavage sequences can be chosen for particular cell types. The efficiency of the co-translational cleavage can be modified to produce the required proportion of cleaved/whole CPs in the assembled VLP.

While modifications and improvements may be incorporated without departing from the scope of the invention, embodiments will now be described by way of the following examples and with reference to the accompanying drawings in which:

FIG. 1a shows the structure of a gene for a chimeric protein and of the overcoat vector pTXS.L2a-CP for use in the present invention;

FIG. 1b is a schematic diagram showing the major features of plasmids useful in the methods of the present invention;

FIG. 2 shows a western blot of wild type and chimeric protein taken from leaves of a plant infected by a wild-type and a chimeric virus;

Figure 4A:
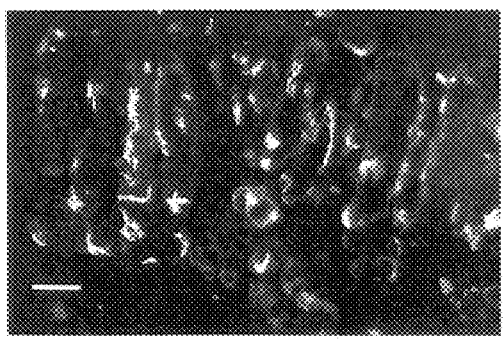
Figure 4B:
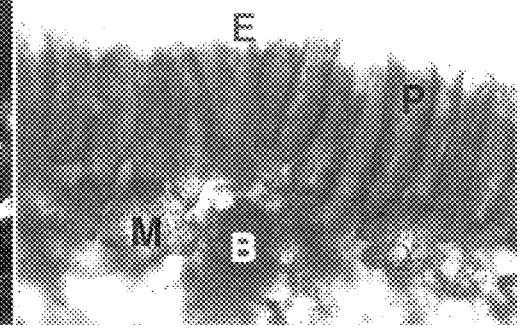
Figure 5:
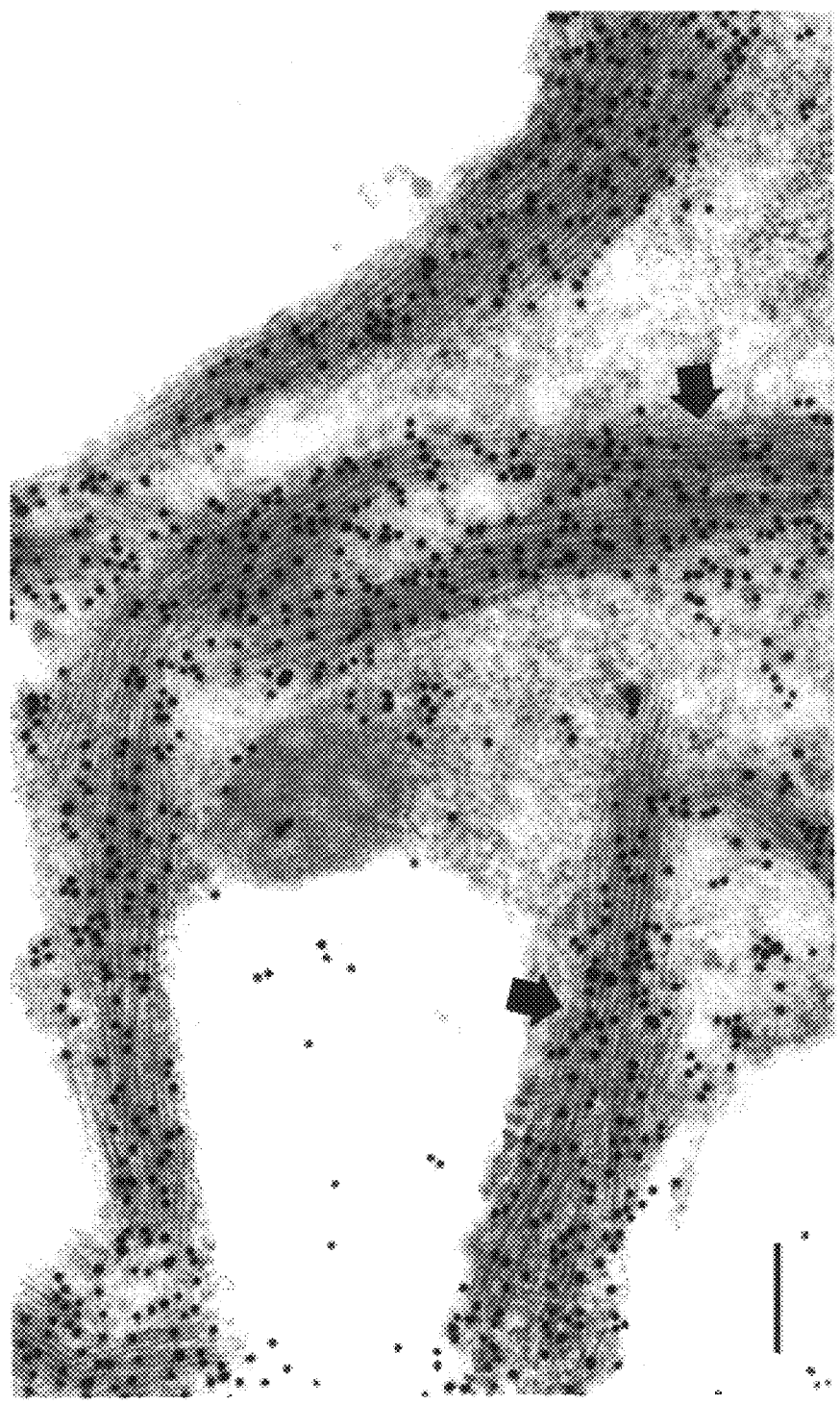
Figures 6A, 6B, 6C:
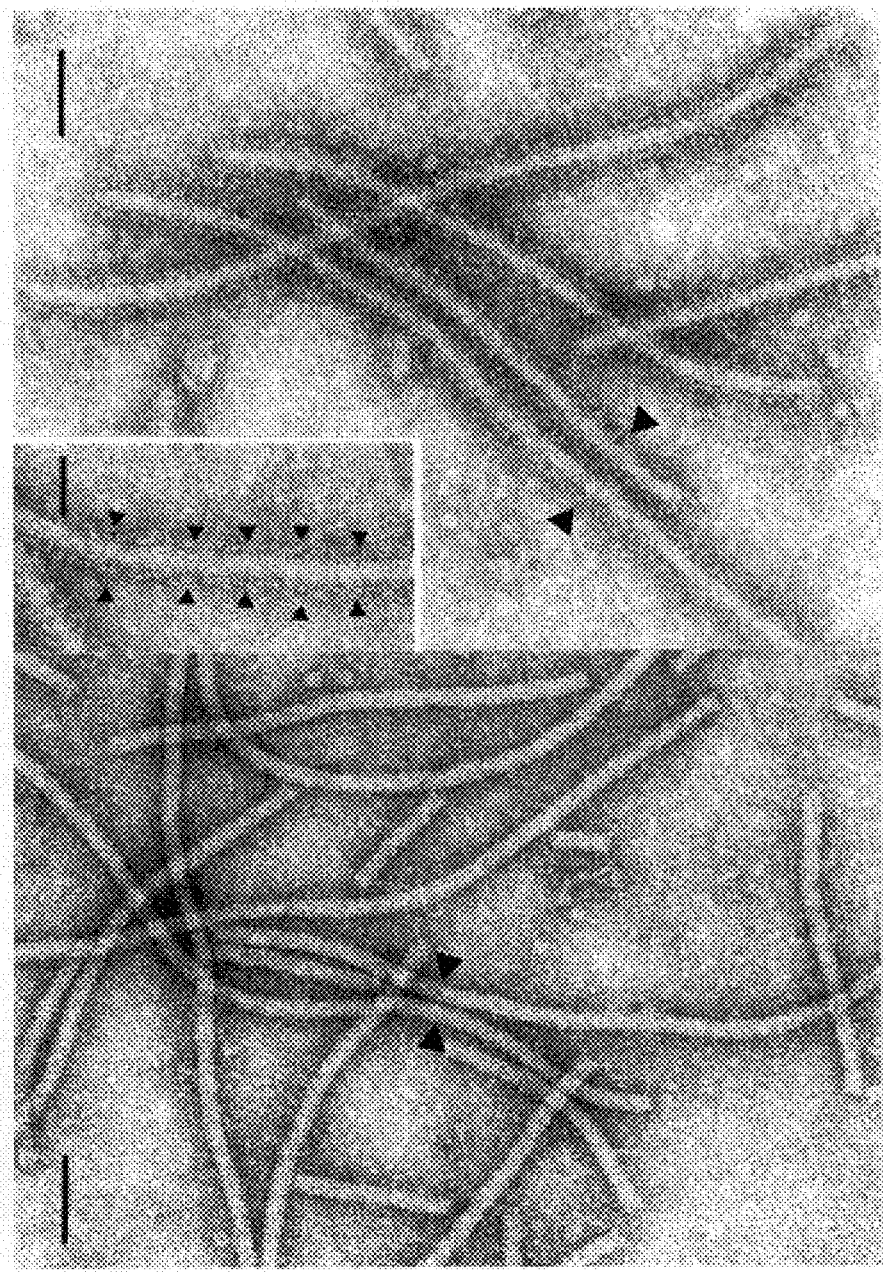
Figure 7:
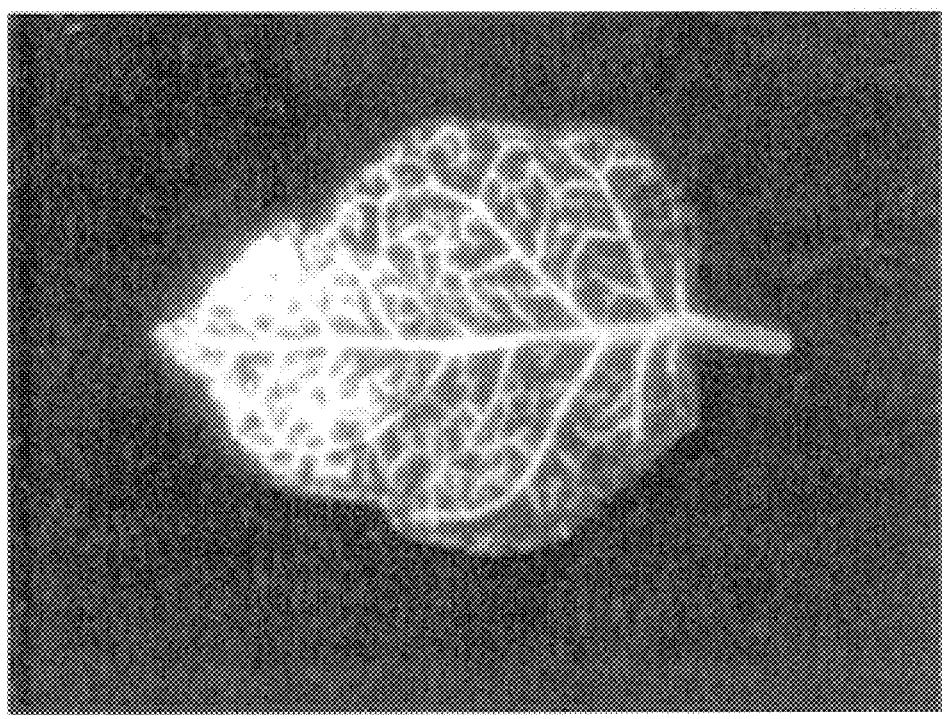
Figure 9:
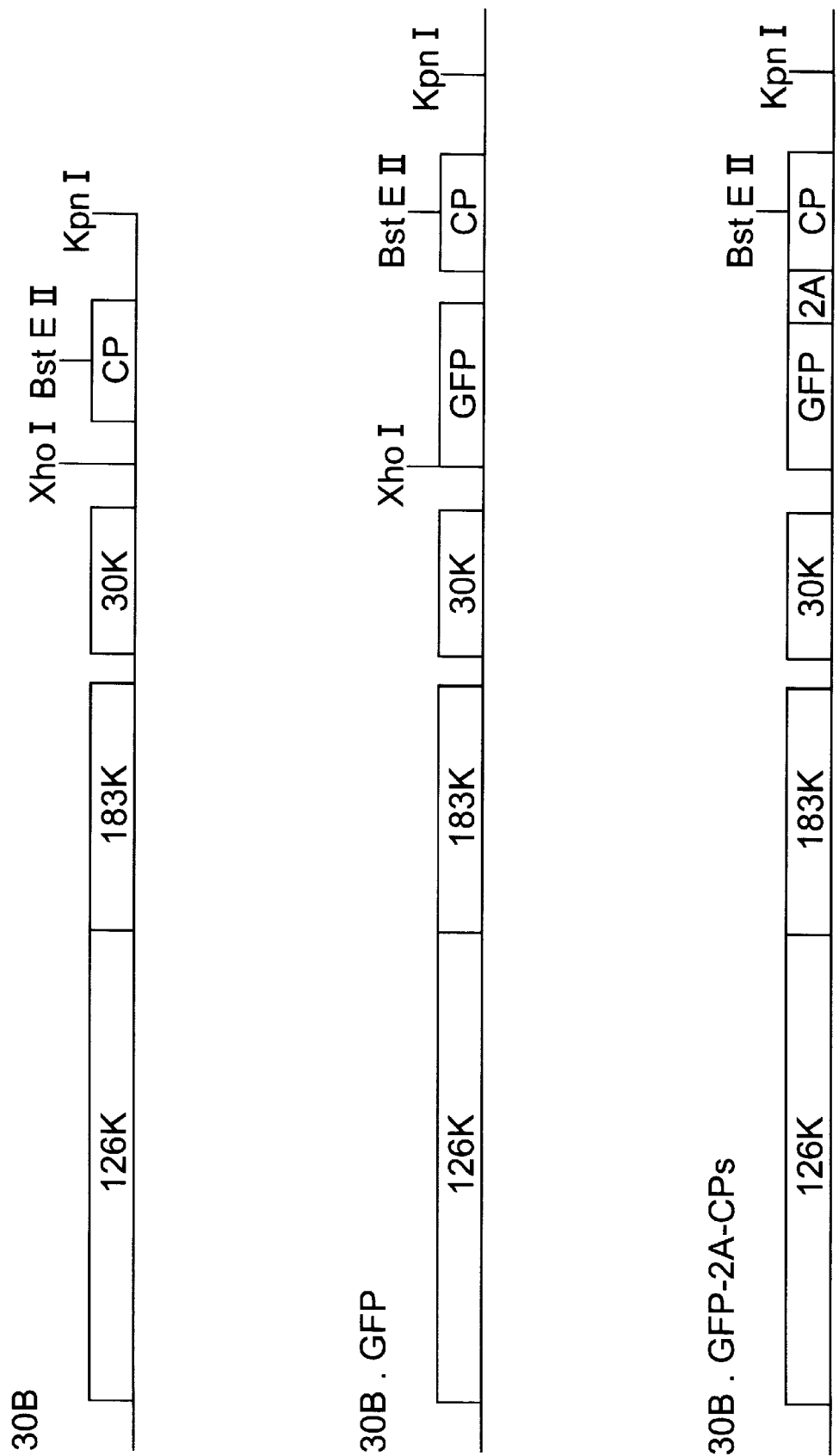
Figure 10:
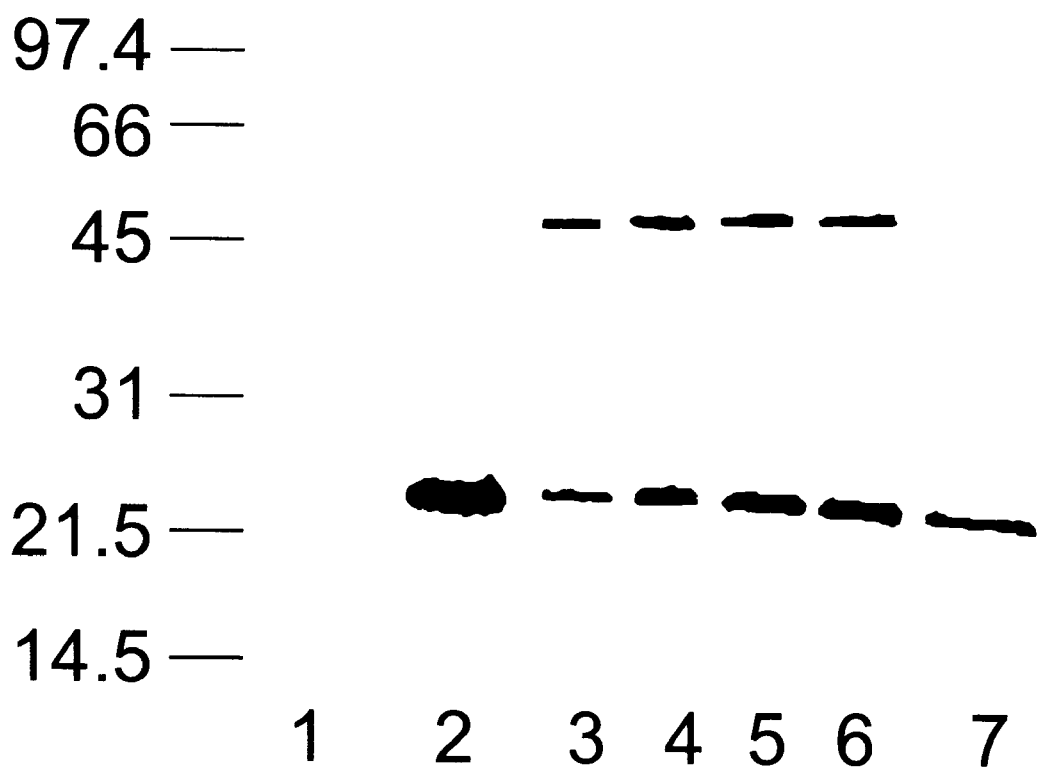

FIGS. 3a, b, c and d show leaves of plants infected with recombinant virus;

FIGS. 4a, b, c, d and e are micrographs illustrating the subcellular distribution of chimeric protein expressed from chimeric virus nucleic acid;

FIG. 5 is an electron micrograph showing aggregation and immuno-gold labelling of chimeric viruses;

FIGS. 6a, b and c are electron micrographs of negatively-stained chimeric viruses;

FIG. 7 is a photograph of a N benthamiana leaf systemically infected with a chimeric virus;

FIG. 8 shows sequence information for LITMUS 39 plasmids used in one example;

FIG. 9 shows a schematic representation of cDNA constructs used in one example;

FIG. 10 shows immunoblot analysis of extracts of leaves probed with anti-CP antiserum; and FIGS. 11a and b show immunoblot analysis of virus prepared from plants infected with a virus-like particle.

EXAMPLE 1

A general strategy for the production of large quantities of recombinant proteins is given below using PVX as an example. A similar strategy could be employed for other flexuous filamentous or rod-shaped viruses. A cDNA clone of potato virus X is first modified to produce fusion proteins between the viral coat protein and proteins with biological activity or other commercial applications. The feasibility of this approach has been demonstrated as described below by creating a translational fusion between the green fluorescent protein (25 kDa) of *Aequorea victoria* (1) and the PVX coat protein (also around 25 kDa). Functional chimeric viruses have also been made which are able to express recombinant genes encoding fusions between the PVX coat protein and the kanamycin resistance protein Neomycin phosphotransferase (25 kDa) and between PVX coat protein and the more complex enzymes β-galactosidase (10–13 kDa) and β-glucuronidase (68 kDa) respectively.

The green fluorescent protein (GFP) from *A. victoria* (1) is a reporter of gene expression in heterologous systems (3–6). GFP has an advantage over other marker proteins in that it can be detected non-invasively, without any requirement for exogenous substrates or co-factors (3) since it fluoresces intrinsically without a requirement for exogenous substrate. In addition, fluorescence of GFP is retained in fusion proteins allowing the subcellular localization of fusion proteins (4).

PCR-mutagenesis of a full-length cDNA copy of the potato virus X genome can be performed to create a synthetic coding sequence comprising the gene coding for the protein of interest, the foot and mouth disease virus 2A protease gene, and the potato virus X coat protein gene. The PVX genome is contained within the known plasmid pTXS (FIG. 1, reference 25).

When reassembled the modified cDNA copy of the viral genome can be used as a template to synthesize in vitro run-off transcripts. Inoculation of transcripts to plants can be performed by manual abrasion of carborundum coated leaves of either *Nicotiana clevelandii* or *N. benthamiana*.

When the above approach was followed using PVX modified to express GFP-CP fusion protein, between two and three days post inoculation the presence of fluorescent regions in the virus infected plants could be observed by eye on inoculated leaves by viewing plants under ultraviolet light. At about ten days post inoculation GFP-mediated fluorescence was detected in systemic (non-inoculated) leaf tissue (FIG. 7). This fluorescence was specific to the green fluorescent protein and was not observed on control plants inoculated with wild-type PVX.

Electron microscopic analysis of viral particles showed a clear increase in particle width in plants infected with the GFP-CP containing virus compared with particles isolated from plants infected with wild-type PVX (FIG. 6).

In the strategy used above, foreign proteins were expressed by fusing them to the amino-terminus of the PVX coat protein. However other sites may be possible, eg carboxy-terminus surface loops on some other rod-shaped or filamentous viruses.

Data from previous studies suggest that fusion of the proteins to the amino terminus of the PVX coat protein is most likely to be successful. Biochemical, immunological and tritium bombardment data suggest a model for the structure of the PVX coat protein (10) in which the N-terminal 33 amino acids form a domain of β-sheet on the outside of the virion. In contrast, the C-terminus of the PVX coat protein, which also forms part of a β-sheet structure, is inaccessible from the outside of the virion and deletions within it do not permit the virus to infect plants systemically.

As an additional optional strategy, the foot and mouth disease virus (FMDV) 2A protease sequence (12) can be positioned between the foreign and coat protein sequences. The FMDV 2A protease is a short 19 amino acid) peptide which acts in cis to cleave the FMDV polyprotein in a co-translational mechanism. This protease has been shown to effect the cleavage of synthetic polyproteins both in vitro and in vivo (13). The inclusion of the 2A protease sequence between the GFP and coat protein can generate a mixed pool of fusion and cleaved proteins in virus infected cells. The presence of free coat protein, generated by 2A protease mediated cleavage, may circumvent this problem by allowing assembly of virions composed of both free (ie cleaved) and fused coat protein subunits.

The formation of virions is an absolute requirement of PVX for systemic infection of plants (15). The demonstration herein that GFP-coat protein fusions do assemble into virions (FIG. 7) and spread indicates that the size of GFP (25 kDa) does not interfere with virion assembly. Fusion proteins which fail to assemble due to size or other constraints can be produced in constructs carrying the FMDV 2A protease, or in plants which are modified to express wild-type coat protein for the particular virus used. The sequence of the 2A protease peptide can be modified to increase or decrease the efficiency of co-translational cleavage.

EXAMPLE 2

This example describes a modified form of PVX which expresses a chimeric gene encoding a fusion between the *Aequorea victoria* green fluorescent protein and the PVX coat protein and assembles into virions that are over twice the diameter of wild-type PVX. The modified virus moves from cell-to-cell and systemically. The example demonstrates the potential of fusions between non-viral protein and virus coat protein for production of high levels of non-viral proteins in plants.

The plasmids used in this work were derived essentially from the plasmid pTXS which contains the PVX genome and a T7 promoter (described in 25). FIG. 1b shows the following main features of the plasmids: the virus RNA-dependent RNA polymerase gene (RdRp); virus genes encoding movement proteins (M1, M2, M3); the virus coat protein gene (CP); promoters from T7 bacteriophage (T7) or for the 35S RNA of CaMV (CaMV35S); the transcriptional terminator of the nopaline synthase gene or *Agrobacterium tumofaciens* and various restriction enzyme sites.

The plasmid pCXA3 was constructed by transfer of the PVX cDNA from pTXS into the plasmid pB1220.5 between the CaMV 35SRNA promoter and the nopaline synthase gene terminator. The plasmid pB1220.5 is similar to the plasmid pB1221.1 but without the GUS gene (described in 27). The junction between the promoter and the PVX cDNA was modified by oligonucleotide directed mutagenesis to the sequence (5')gattoggagagga*gaaaactaaacca(3') (SEQ ID NO:1) in which * denotes the most 3' non-transcribed position in the promoter sequence and the most 5' transcribed position in the viral genome (28). Construction of the pVX201 vector from pCXA3 and pPC2S exploited unique restriction sites at positions 4945 (Apa1) and 6302 (Xho1) of the PVX cDNA (25).

GFP cDNA was PCR-amplified with primers (5') gccaatcgatcatgagtaaaggag(3') (SEQ ID NO:2) on the positive strand and (5') ggaagtcgacacatttatttg(3') (SEQ ID NO:3) from the negative strand. The bold type represents the initiation and termination codons of the GFP gene (29). The underlined type represents ClaI and SalI sites used to introduce the PCT-amplified sequence into pPVX201 to generate pVX204. The plasmid pTXS.GFP was made by substitution of the region of pPVX204 containing the GFP sequence into the homologous region of pPC2S.

The plasmid pTXS.GFP carries a full-length cDNA copy of the potato virus X (PVX) genome into which the GFP gene has been inserted. Inoculation of plants with transcripts synthesized in vitro form pTXS.GFP results in the expression of free GFP in infected cells (5). We prepared a derivative of pTXS.GFP, pTXS.GFP-CP, to create a translational fusion between the carboxyterminus of the GFP and the amino-terminus of the PVX coat protein (CP). pTXS.GFP was used as a template to produce the GFP-2A-CP fusion gene by overlap extension PCR using flanking oligonucleotides complementary to the PVX genome and mutagenic oligonucleotides to incorporate the 2A protease coding sequence. Amplified product was subcloned into pTXS.GFP as a 1.5 kbp fragment using the unique restriction sites ClaI and XhoI to give pTXS.GFP-CP. FIG. 1a shows a schematic representation of viral cDNAs used to synthesize infectious run-off transcripts for the GFP-2A-CP fusion gene. The predicted Mrs of the four viral proteins common to all constructs are indicated (K=kD). The polypeptide chain lengths of the CP, GFP and 2A protease (2A) enclosed by the constructs are shown. The bars indicate the position of the subgenomic promoter for the CP. TXS= wild-type PVX; TXS.GFP=PVX modified to express free GFP from a duplicated subgenomic promoter; TXS.GFP-CP=PVX modified to express the GFP-2A-CP fusion protein.

Because the GFP and PVX CP are of similar sizes, having molecular weights of 26.9 kD and 25.1 kD respectively, it was expected that in a homogenous population of fusion protein steric effects would prevent virion formation. Assembly of fusion protein into virions might be facilitated by the presence of a pool of free CP. Therefore the GFP and CP nucleotide sequences in pTXS.GFP-CP were separated by sequence coding for sixteen amino acids from the foot-and-mouth disease virus (FMDV) 2A peptide. The 2A region of FMDV mediates a primary (co-translational) processing event between the 2A and 2B regions of the FMDV polyprotein (12) that results in inhibition of peptide bond formation (13).

In vitro run-off transcripts (14), synthesized from pTXS.GFP and pTXS.GFP-CP (plasmids were linearized with Spe 1 prior to in vitro transcription reactions as described in reference 14), were infectious when inoculated to plants; virus derived from transcript-infected plants is subsequently referred to as pVX.GFP and PVX.GFP-CP respectively.

Following inoculation of either *Nicotiana clevelandii* or *N. benthamiana*, both PVX.GFP and PVX.GFP-CP caused the development of green fluorescent regions which were first detectable by eye under UV illumination between two and three days post inoculation (FIGS. 3A, C). Subsequent long-distance movement of the virus to developing leaves led to the appearance of green fluorescence in systemically infected leaves (FIGS. 3B, D). The rate at which fluorescent regions spread on inoculated leaves was slower in PVX.GFP-CP infected plants than PVX.GFP infected plants and the appearance of fluorescence in systemically infected leaves was delayed in plants infected with PVX.GFP-CP compared with PVX.GFP infected plants.

FIG. 3 shows leaves of *N. benthamiana* infected with either PVX.GFP (A, B) or PVX.GFP-CP (C, D). Leaves were viewed under UV illumination (365 nm) generated from a Blak Ray B100-AP lamp (Ultra-Violet Products) and photographed using a Wratten 58 filter to eliminate chlorophyll auto-fluorescence. The pattern of virus spread in both cases is similar. A and C identify inoculated leaves showing the development of characteristic circular legions. B and D identify systemically infected leaves showing fluorescence associated predominantly with the leaf veins. The developing leaf (D) was undergoing the sink-source transition (20) resulting in lack of virus movement into the apical portion of the leaf.

FIG. 4a is a confocal fluorescence image of a systemically infected leaf in transverse section showing the location of PVX.GFP-CP containing viroplasms within individual cells of the leaf. 4b is a bright field image of section shown in (A) showing the typical arrangement of epidermis (E), palisade (P) and mesophyll(M) cells. A vascular bundle (B) is also present (scale=50 μm). 4c is a confocal image of palisade cells from a leaf systemically infected with PVX.GFP-CP showing the GFP-containing viroplasma (V) assembled into cage-like structures (scale=5 μm). 4d shows a leaf trichome systemically infected with PVX.GFP, in which the GFP is associated with the nucleus (N) and the cytoplasm. 4e shows a leaf trichome systemically infected with PVX.GFP-CP, in which the GFP is predominantly targeted to viroplasma (V) within individual trichome cells (scale=10 μm).

Figure 4C:
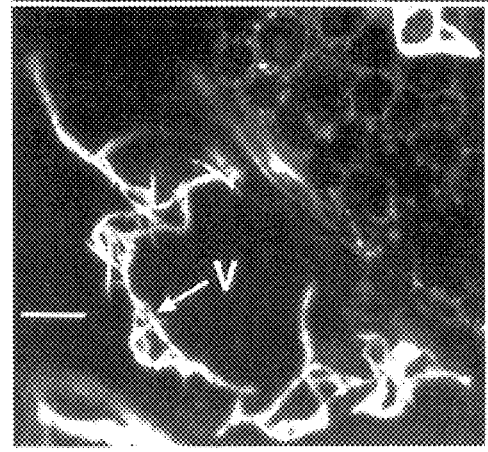
Figure 4D:
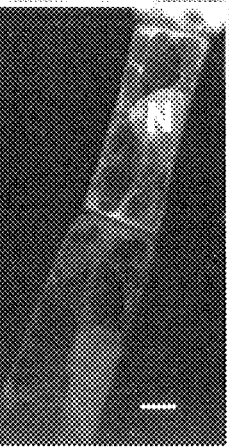
Figure 4E:
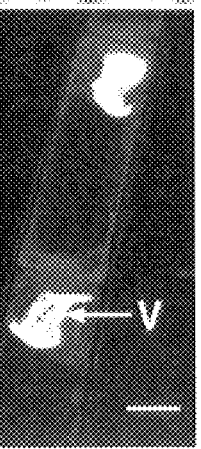

In systemically infected (ie non-inoculated) leaves both PVX.GFP and PVX.GFP-CP moved from the phloem into surrounding bundle sheath and mesophyll cells and eventually into the epidermis (FIGS. 4A, B). Under the confocal microscope transverse sections of the systemically infected leaves showed that in PVX.GFP-CP infected cells green fluorescence was detected predominantly in viroplasms, cytoplasmic structures comprising aggregated viral particles that often appeared as continuous cage-like structures within the cell (FIGS. 4C, 5). By contrast, in PVX.GFP infected cells, the green fluorescence was associated with nuclei and showed a relatively uniform distribution throughout the cytoplasm. This difference in the subcellular distribution of the GFP was seen clearly in leaf trichome cells (FIGS. 4D, E).

The distribution of fluorescence suggested that the majority of GFP produced in PVX.GFP-CP infected plants was still fused to the CP and that these fusion proteins were assembling into virions, which subsequently formed viroplasms.

Western blotting of protein extracts from inoculated N. clevelandii leaves, probed with CP specific antiserum (16), showed that most of the immunoreactive protein in PVX.GFP-CP infected plants comprised the fusion protein. Protein extracts were prepared by grinding leaf tissue in two volumes (w/v) protein extraction buffer (15). An equal volume of 2× SDS load buffer was added and the extracts were boiled for two minutes. Proteins were electrophoresed, blotted to nitrocellulose and probed with rabbit polyclonal anti-PVX CP antiserum as described previously (16). FIG. 2 illustrates the data obtained. Protein was prepared from mock inoculated control plants (lane 2), or from plants inoculated with in vitro transcripts synthesized from plasmid DNAs (TXS=lane 1; TXS.GFP-CP=lane 3; TXS.GFP=lane 4). Mrs of native CP, the GFP-2A-CP fusion protein and CP released by 2A protease mediated cleavage are 25.1, 53.2 and 24.8 kD respectively. The Mrs of standards are shown to the left of FIG. 2 in kD.

The low level of smaller immunoreactive protein detected in PVX.GFP-CP infected tissue is assumed to result from processing of the fusion protein mediated by the FMDV 2A peptide rather than from contamination with virus deletion mutants as similar ratios of fusion to free protein were observed in all other samples analyzed and RT-PCR analysis of the same samples used for protein analysis showed no evidence of deleted forms of the viral genome (17). In addition when blots were probed with GFP specific antiserum the ratio of free protein to fusion protein was the same as that observed using anti-CP antiserum (17).

In order to determine the subcellular location of the viral CP ultrathin sections of inoculated leaves were prepared for immuno-gold labelling, using a polyclonal antibody to the PVX CP. Leaf tissues were fixed and embedded in Araldite (TM) resin for immuno-gold labelling as described previously (17). Ultrathin sections on nickel grids were labelled using polyclonal rabbit antiserum to the PVX CP followed by goat anti-rabbit gold conjugate (GAR-15 nm, Amersham International). Aggregation of the filamentous virions into viroplasms is marked with arrows in FIG. 5. Dense gold labelling was predominantly associated with the viroplasms in both PVX.GFP and PVX.GFP-CP infected cells. The pattern of virus aggregation seen in the electron microscope for both PVX.GFP-CP (FIG. 5) and PVX.GFP was remarkably similar to the cages of viroplasm seen with PVX.GFP-CP under the confocal microscope (FIG. 4c).

For negative staining, virus particles were trapped from virus infected sap extracts by immuno-sorbent electron microscopy (18) using anti-PVX CP antiserum, and stained with 2% sodium phosphotungstate (pH 7 ).

Analysis of negatively stained virus samples under the electron microscope revealed that PVX.GFP-CP virions were decorated along their length with globular extensions (FIGS. 6a, b). FIG. 6c shows negatively stained virus rods isolated from PVX.GFP infected plants (scale=50 nm). Differences in virion diameter are seen most clearly where virions are aligned in parallel (a and c, large darts). In FIG. 6b small globular extensions (small darts) are apparent along the length of the PVX.GFP-CP virus (scale=25 nm). The PVX.GFP-Cp virions had a mean diameter of 29.7 nm, more than twice the diameter of PVX.GFP virions (12.6 nm; FIG. 6c).

A modified form of PVX.GFP-CP, in which the FMDV 2A peptide sequence carries three amino acid substitutions, introduced to prevent processing of the polyprotein, was unable to move from cell-to-cell and did not give rise to fluorescent viroplasms. Infections with this mutant were restricted to single epidermal cells and fluorescence was detected uniformly throughout the cytoplasm and in association with nuclei, as observed for PVX.GFP infections (17), suggesting that the presence of free CP is essential for either initiation of elongation of virions.

The fluorescence generated by the GFP attached to virions was intense, allowing rapid detection of viral aggregates within individual living cells. Furthermore, confocal microscopy allowed the noninvasive imaging of the pathway of cell-to-cell movement of virus-GFP constructs, pinpointing the specific cell types in which virus accumulated. For confocal imaging leaves were excised from the plant and sectioned transversely into 200 μm slices using a vibrotome. The sections were immediately mounted in water and viewed under a Bio-Rad MRC 1000 confocal laser scanning microscope at an excitation wavelength of 488 nm using a krypton-argon laser.

Previous descriptions of assembly competent plant RNA viruses carrying CP extensions have involved small oligopeptide fusions (19). The data presented in this example suggest that the system described could be used for the production of proteins that are at least as large as the viral CP of PVX.

The strategy described to generate GFP-coat protein fusions can be easily applied to proteins other than GFP. We modified the plasmid pTXS.GFP-CP which carries the GFP-2A-CP fusion protein gene to enable the facile insertion of novel coding sequence as a fusion to the 2A-CP cassette. This modified plasmid, pTXS.L2a-CP shown in FIG. 1a (deposited under No NCTC 12918 at the National Collection of Type Cultures at 61 Colindale Avenue, London NW9 5HT on Oct. 18, 1995) carries a series of unique restriction enzyme recognition sites (Clal, Egal, Smal, Ehel) or polylinker that replaces the GFP coding sequence of pTKS.GFP-CP. By digesting the vector pTXS.L2a-CP at one or more of the polylinker restriction enzyme sites it is possible to insert the coding sequence for any given protein such that a fusion protein gene is created comprising the novel gene, the FMDV 2A peptide and the PVX coat protein as a translational fusion.

The plasmid vector pTXS.L2a-CP was prepared by PCT-based mutagenesis of the plasmid pTXS.GFP-CP using standard techniques (26). The oligonucleotide 2aL5' was annealed to the primer 2aL3' and extended with T4 DNA polymerase.

The sequence of primers used was

```
2aL5'(SEQ ID NO:4):  5'  TCG GCC GTC CCG GGG GCG 3'
                         ||| ||| ||| ||| ||| |||
2aL3'(SEQ ID NO:5):  3'  AGC CGG CAG GGC CCC CGC GGT TAA AAC TGG AAG

AAT TCG AAA 5'
```

The extended product was gel purified and cloned into the plasmid M13RK8.2 (30). An Eag 1/Afl 11 fragment was excised from the resulting plasmid and cloned between the same sites of the plasmid pTXS.GFP-CP in place of the GFP gene.

Thus, the nucleotide sequence of the new linker in pTXS.L2a-CP is

```
                          Cla1     Eag1      Sma1     Ehe1

/_____\  /_____\   /_____\ /____\
Nts(SEQ ID NO:6):        AT CGA TCC GGC CGT CCC GGG GGC GCC AAT TTT

Amino acids(SEQ ID NO:7):                   Pro Gly Gly Ala Asn Phe
```

Insertion of foreign genes into the pTXS.P-CP polylinker are most easily performed by PCR amplification of the foreign gene using oligonucleotides designed to incorporate appropriate restriction enzyme recognition sites at the 5'- and 3'-termini of the foreign coding sequence such that the gene for the synthetic polyprotein comprises a single open reading frame. We have demonstrated the utility of this approach using the gene encoding neomycin phosphotransferase (NPT) which confers resistance to the antibiotic kanamycin and is present in most commercially available plasmids as a selection tool. The 0.73 kb (NPT) coding sequence was inserted into the polylinker of pTXS.P-CP to give the plasmid pTXS.NPT- CP. Transcripts synthesized in vitro from the pTXS.NPT-CP template were infectious on plants and the virus moved both locally and systemically. Assembly of PVX.NPT-CP virions results in "overcoat" virus particles carrying the NPT protein on the surface of the virions.

EXAMPLE 3

A plasmid containing the tobacco mild green mosaic virus (TMGMV) coat protein (CP) gene and 3' untranslated region (UTR) was produced to facilitate the production of green fluorescent protein (GFP), foot-and-mouth disease virus 2A, TMGMV CP gene fusions. A 955 base pair (bp) fragment containing the TMGMV CP and 3' UTR was PCR amplified from the plasmid 30B (W. O. Dawson, Citrus Research and Education Center) using the primers TMGMV-CP-Apa (5' CAA-TGG-GCC-CTA-TAC-AAT-CAA-CTC-T 3'(SEQ ID NO: 8)) and M13-Reverse (5' AGC-GGA-TAA-CAA-TTT-CAC-ACA-GGA 3'(SEQ ID NO: 9)). The primer TMGMV-CP-Apa was designed to mutagenize the sequence coding for the initiating methionine and first proline codon of the TMGMV CP to an ApaI restriction enzyme site. This results in the conversion of the methionine codon to a glycine codon, but maintains the proline codon. The 837 bp fragment released by digestion of the PCR amplification product with the restriction endonucleases ApaI and KpnI was cloned into the 3322 bp fragment released by digestion of pSL1180 (Pharmacia) digested with the same restriction endonucleases and treated with calf intestinal alkaline phosphatase. The resulting plasmid was named pSL.TMGMV-CP-UTR.

CFP-2A-TMGMV CP gene fusions were produced by cloning DNA fragments containing GFP-2A fusions into pSL.TMGMV-CP-UTR adjacent to the codon for the first proline in the TMGMV CP gene. A selection of LITMUS 39 (New England Biolabs) based plasmids containing GFP-2A-potato virus X CP gene fusions were used as sources for the GFP-2A gene fusion.

The nucleotide sequence and amino acids encoded by the different LITMUS 39 based plasmids between the carboxy-terminal lysine codon of the GFP gene and the amino-terminal proline codon of the PVX CP gene are shown in FIG. 8. The nucleotide and amino acid sequences of the portion of plasmid pLit.GFP-2A$_{23H}$-CP illustrated in FIG. 8 are designated SEQ ID No: 12 and SEQ ID No: 13, respectively. The nucleotide and amino acid sequences of the portion of plasmid pLit.GFP-2A$_{16H}$-CP illustrated in FIG. 8 are designated SEQ ID No: 14 and SEQ ID No: 15, respectively. The nucleotide and amino acid sequences of the portion of plasmid pLit.GFP-2A$_{16K}$-CP illustrated in FIG. 8 are designated SEQ ID No: 16 and SEQ ID No: 17, respectively. The nucleotide and amino acid sequences of the portion of plasmid pLit.GFP-2A$_{58K}$-CP illustrated in FIG. 8 are designated SEQ ID No: 18 and SEQ ID No: 19, respectively.

These plasmids contain a variety of sequences coding for different 2A amino acid sequences between the carboxy-terminal lysine codon of GFP and the first proline codon of the PVX CP. Fragments of between 900 and 1050 bp were PCR amplified from the plasmids pLit, GFP-2A$_{16H}$-CP, pLit.GFP-2A$_{16K}$-CP, pLit.GFP-2A$_{23H}$-CP and pLit.GFP-2A$_{58K}$-CP using the primers (GFP-5'-Sal (5' TCA-ATC-GTC-GAC-ATG-AGT-AAA-GGA-GAA-GAA 3'(SEQ ID NO: 10)) and N3#4 (5' TGT-ACT-AAA-GAA-ATC-CCC-ATC-C 3'(SEQ ID NO: 11)). The primer GFP-5'-Sal introduces a SalI restriction enzyme site upstream of the initiating methionine codon of the GFP gene. Fragments containing the GFP gene fused to the different 2A sequences were released by digestion of the PCR amplification products with SalI and ApaI and ligated into the large fragment released by digestion of pSL.TMGMV-CP-UTR with the same restriction enzymes and treated with calf intestinal phosphatase. The resulting plasmids were digested with SalI and BstEII and the released fragments containing the GFP-2A-TMGMV CP gene fusion and TMGMV UTR were introduced into the plasmid 30B digested with XhoI and BstEII to regenerate full-length TMV based clones. Thus the final clones comprise wild-type TMV strain U1 sequence up to position 5757 in the CP gene, with the exception of a mutagenized CP initiating methionine codon, followed by a short polylinker sequence, the GFP-2A-TMGMV CP gene fusions and the TMGMV 3' UTR.

FIG. 9 shows a schematic representation of viral cDNA constructs used in this example. Boxes represent coding sequences. The genes for the three viral proteins common to all constructs are indicated by their predicted Mr values (K=kDa). The genes for the green fluorescent protein, 2A oligopeptide and TMGMV CP are indicated by GFP, 2A and CP respectively. Restriction enzyme sites used in the cloning procedures are indicated above.

In vitro run-off transcripts were synthesized from KpnI linearized plasmids p30B.GFP-2A$_{16H}$-CP, p30B.GFP-2A$_{16K}$-CP, p30B.GFP-2A$_{23H}$-CP, p30B.GFP-2A$_{58K}$-CP and p30B.GFP, a derivative of p30B that has had the GFP gene introduced into the unique XhoI site of P30B, which expresses free GFP. The transcripts derived from all the plasmids were infectious when inoculated onto *Nicotiana benthamiana* plants; virus derived from transcript-infected plants is referred to subsequently by the name of the progenitor plasmid without the "p" prefix. Following inoculation, all the viruses caused the development of fluorescent regions which were first detectable by eye under UV illumination between three and four days post inoculation. Subsequent long distance movement of the virus led to the appearance of green fluorescence in systemically infected leaves. The appearance of fluorescence in systemically infected leaves occurred at a similar time, nine days post inoculation, for plants infected with 30B.GFP, 30B.GFP-2A$_{16H}$-CP and 30B.GFP-2A$_{16K}$-CP, but was delayed for 30B.GFP-2A$_{23H}$-CP and 30B.GFP-2A$_{58K}$-CP.

Western blotting of protein extracts were systemically infected *N. benthamiana* leaves, probed with rabbit polyclonal antisera raised against TMV CP (FIG. 10), detected two protein species in each of the 30B.GFP-2A-CP infected samples. This result indicated that the modified viruses were producing a GFP-2A-CP fusion protein, the in vivo processing of which resulted in the production of a GFP-2A fusion protein and free TMGMV CP. For 30B.GFP-2A$_{16H}$-CP, 30B.GFP-2A$_{16K}$-CP and 30B.GFP-2A$_{58K}$-CP the majority of CP related protein produced was in the unfused form. Protein was prepared from mock-inoculated control plants (lane 1) or form plants inoculated with in vitro transcripts synthesized from plasmid DNAs (p30B.GFP, lane 2; p30b.GFP-2A$_{23H}$-CP, lane 3; 30B.GFP-2A$_{16H}$-CP, lane 4; 30B.GFP-2A$_{16K}$-CP, lane 5; 30B.GFP-2A$_{58K}$-CP, Lane 6). Lane 7 contains 125 ng of TMGMV CP. The predicted Mr values of TMGMV CP, GFP and GFP-2A-CPs are 17.5 kDa, 26.9 kDa and between 46 and 52 kDa, respectively. The Mr values of standards ($\times 10_{-3}$) are shown on the left.

The observation that the modified viral constructs were capable of rapid systemic movement like 30B.GFP suggested that they were also capable of virus particle formation. To confirm that this was the case homogenates were prepared by grinding fluorescent inoculated leaf tissue from plants infected with 30B.GFP and 30B.GFP-2A$_{23H}$-CP in a "mini-mortar" with 50 mM phosphate buffer pH 6.5. The homogenates were applied to a carbon coated grid and stained with 2% sodium phosphotungstate pH 6.5 prior to observation in the electron microscope. 30B.GFP-2A$_{23H}$-CP was found to produce rod-shaped particles like those produced by 30B.GFP. To test whether the particles produced by 30B.GFP-2A$_{23H}$-CP had incorporated GFP-2A-CP fusion protein as well as free TMGMV CP immunotrapping (Roberts 1986, in Electron microscopy of proteins, Academic Press) was performed with rabbit polyclonal antisera raised against GFP and TMV.CP. While 30B.GFP infected tissue showed enhanced trapping with the TMV-CP antisera, but not with the GFP antisera, 30B.GFP-2A$_{23H}$-CP infected tissue showed enhanced trapping with both antisera (Table 1). This result suggested that the modified virus was capable of incorporating GFP-2A-CP fusion protein into particles.

TABLE 1

| Coating antiserum | Number of particles/1000 $\mu m^2$ | |
|---|---|---|
| | 30B.GFP | 30B.GFP-2A$_{23H}$-CP |
| None | 223 +/− 57.0 | 3.5 +/− 1.33 |
| TMV CP | 4690 +/− 1200 | 58.0 +/− 3.16 |
| GFP | 112 +/− 9.45 | 67.5 +/− 15.2 |

To confirm this a virion extraction (Kearney et al, in Plant Molecular Biology Manual L1:1–16, Kluwer Academic Publisher) was performed on fluorescent, systemically infected tissue of plants infected with 30B.GFP-2A$_{16H}$-CP. Western blot analysis (FIG. 11) of the virus preparation with GFP (B) and TMV CP (A) antisera demonstrated that the virus contained TMGMV CP and CGP-2A-CP fusion protein but no GFP-2A fusion protein. Mr values shown on left of FIG. 11 ($\times 10^{-3}$) Thus the GFP-2A-CP fusion protein was assembled with free TMGMV CP into virus particles.

The advantages of the invention are as follows:

(i) Standard purification procedures exist (e.g. polyethylene glycol precipitation and centrifugation) for these highly stable virus particles to remove plant proteins and cellular debris and to give an extremely pure suspension of plant virus particles. Plant viruses are innocuous to humans, ingestion experiments have already revealed that they pass straight through the intestine undamaged.

(ii) By attaching the foreign protein to each (or a subset of) coat protein subunits optionally with a suitable cleavage-sensitive linker sequence will allow, following virus purification from the infected plant sap, foreign protein to be released into free solution simply by incubation with the appropriate proteolytic enzyme. The released virus particles remain stable and of high molecular weight so that they can be separated from the short peptide either by simple dialysis procedures (continuous flow type), or by differential centrifugation or selective precipitation.

(iii) Yields of cleaved foreign protein from such a system could reach 50% or more of the total weight of virus recovered. Each helical virus particle has 95% of its weight as coat protein, and each coat protein subunit has a molecular weight of approximately 25 kD. In the model system already developed the green fluorescent protein also has a molecular mass of approximately 25 kD. Yields of potato virus X can be extremely high (up to 5 mg/kg wet weight of infected leaf after several weeks).

(iv) The flexibility of scale that can be achieved in plants is also attractive in terms of reducing the cost of protein production and avoids the need for high level capital investment such as in animal or microbial cell culture facilities.

(v) The use of set-aside land and/or discredited crops such as tobacco for the alternative production of highly prized, pharmaceutically active proteins would lead to considerable added value in the periagricultural sector.

REFERENCES

The following documents referred to in the text are incorporated herein by reference:

1. B. L. Epel, Plant Mol. Biol. 26, 1343–1356 (1994): W. J. Lucan & R. L. Filbertson, Annu. Rev. Phytopathol. 32, 387–411 (1994); B. G. McLean, W. Waigmann, V. Citovsky & P. Zambryski, trends Microbiol. 1, 105–109 (1993).
2. D. C. Prasher, V. K. Eckenrode, W. W. Ward, F. G. Prendergast & M. J. Cormier, Gene 111, 229–233 (1992).
3. M. Chalfie, Y. Tu, G. Euskirchen, W. W. Ward & D. C. Prasher, Science 263, 802–805 (1994).
4. S. Wang & T. Hazelrigg, Nature 369, 400–403 (1994).
5. D. C. Baulcombe, S. Chapman & Santa Cruz, Plant J.7, 1045–1053 (1995).
6. R. P. Niedz, M. R. Sussman & J. S. Satterlee, Plant Cell Rep. 14, 403–406 (1995).
7. S. Chapman, T. Kavanagh & D. C. Baulcombe, Plant J. 2, 549–557 (1992).
8. H. B. Scholthof, T. J. Morris & A. O. Jackson, Mol. Plant-Microbe Interact. 6, 309–322 (1993).
10. L. A. Bartova et al., Virology 188, 175–180 (1992).
11. R. Koenig & L. Torrance, J. Gen. Virol 67, 2145–2151 (1986).
12. M. D. Ryan, A. M. Q. King & G. P. Thomas, J. Gen. Virol. 72, 2727–2732 (1991).
13. M. D. Ryan and J. Drew, EMBO J. 13, 928–933 (1994).
14. T. Kavanagh et al., Virology 189, 609–617 (1992).
15. S. Chapman, G. Hills, J. Watts & D. C. Baulcombe, Virology 191, 223–230 (1992).
16. C. Davies, G. Hills & D. C. Baulcombe, Virology 197, 166–175 (1993).
17. C. Fasseas, I. M. Roberts & A. F. Murant, J. Gen. Virol. 70, 2741–2749 (1989).
18. I. M. Roberts, in Electron microscopy of proteins: 5. Viral structure, J. R. Harris & R. W. Horne, Eds. (Academic Press, New York, 1986), pp 293–357.
19. H Hamamoto et al., BIO/TECHNOLOGY 11, 930–932 (1993); R. Usha et al., Virology 197, 366–374 (1993); C. Porta et al., Virology 202, 949–955 (1994); T. H. Turpen et al., BIO/TECHNOLOGY 13, 53–57 (1995).
20. R. Turgeon, Annu. Rev. Plant Physiol. Plant Mol. Biol. 40, 119–138 (1989).
21. Abouhaidar, M. G. and Lai, R. (1989) J. Gen. Virol. 70, 1871–1875.
22. Kokyakov, V. N. Harwig, S. S. L., Panyutich, E. A., Schevchenko, G. M. A., Shamova, O. V., Korneva, H. A. and Lehrer, R. I. (1993) FEBS letters 327, #2, 231–236.
23. Pardi, A., Zhang, X-L., Selsted, M. E., Skalicky, J. J. and Yip, P. F. (1992) Biochemistry 31, 11357–11364.
24. Lehrer, R. J. Ganz, T. and Selsted, M. E. Defensins: Endogenous Antibiotic Peptides of Animal Cells. (1991) Cell 64 229–230.
25. Kavanagh, T Goulden, M Santa Cruz, S., Chapman, S., Barker, I and Baulcombe, D. C. (1992) Virology, 189, 609–617.
26. Sambrook et al (1989. Molecular cloning, a laboratory manual. Cold Spring Harbor Laboratory.
27. Jefferson et al (1987) Plant Vol. Biol. Pep. 5, 387–405.
28. Guilley et al (1982) Cell 30, 763–773.
29. Prasher et al (1992) Gene 111, 229–233.
30. Waye et al (1985) Nucleic Acids Res. 13(23) 8561–8571.

What is claimed is:

1. A method of producing a chimeric protein, the method comprising:
   a) providing a recombinant first virus or pseudovirus containing a polynucleotide encoding a chimeric protein having a first, viral coat protein, portion and a second, foreign peptide or protein, portion, wherein said second portion consists of over 25 amino acids and includes a sequence able to mediate automatic cleavage of a proportion of the total amount of chimeric protein at a pre-determined site therein to yield a particle-forming moiety and a target peptide moiety, wherein said particle-forming moiety and said uncleaved chimeric protein are capable of co-assembly into a rod-shaped virus or pseudovirus such that any second portion is disposed on the exterior surface of the assembled virus or pseudovirus;
   b) infecting a host cell with the first virus or pseudovirus; and
   c) allowing replication and expression of the polynucleotide in the host cell to produce said chimeric protein, said particle-forming moiety and said target moiety.

2. A method according to claim 1, including the step of allowing self-assembly of said chimeric protein, said particle-forming moiety and a copy of said polynucleotide to form a product virus or pseudovirus capable of replicating and assembling in plants.

3. A method according to claim 2, wherein the product virus or pseudovirus particle comprises a mixture of chimeric protein and wild-type coat protein.

4. A method according to claim 2, including the step of purifying the product virus or pseudovirus from the host cell.

5. A method according to claim 4, including the step of cleaving at least a part of the second portion from the product virus or pseudovirus after purification of the product virus or pseudovirus from the host cell.

6. A method according to claim 1, wherein a linker peptide is incorporated between the first and second portions.

7. A method according to claim 1, including the step of purifying protein derived from the second portion from the host cell after replication and expression of the polynucleotide in the host cell.

8. A method according to claim 1, wherein the product virus or pseudovirus is a plant virus or a pseudovirus thereof.

9. A method according to claim 8 wherein the virus or pseudovirus is selected from the group consisting of potexvirus, potyvirus or pseudoviruses thereof.

10. A method according to claim 1, wherein the product virus or pseudovirus is modified potato virus X or a pseudovirus thereof.

11. A method according to claim 1, wherein the second portion is located at or adjacent to the N-terminus of the first portion.

12. A method according to claim 1, wherein the second portion is selected from the group consisting of a proteinaceous diagnostic reagent, an antibiotic, a therapeutic agent, a pharmaceutically active agent, an antigenic epitope and a food supplement.

13. A method according to claim 1, wherein the product virus or pseudovirus has a pitch of helix of more than 2 nm.

14. A method according to claim 1, wherein the product virus or pseudovirus is flexuous.

15. A method according to claim 1, wherein in step b the host cell is infected with a first virus or pseudovirus particle which is a plant virus or a pseudovirus thereof.

16. A method according to claim 1, wherein in step b the host cell is infected with a first virus or pseudovirus which is modified potato virus X or a pseudovirus thereof.

17. A method according to claim 1, wherein the second portion or a peptide derived therefrom has a molecular weight in excess of 10 kDa.

18. A chimeric protein produced by a method according to claim 1.

19. A method according to claim 1, including the step of purifying target moiety from the host cell.

20. A method according to claim 1 wherein the second portion has over 30 amino acids.

21. A method according to claim 1 wherein said automatic cleavage occurs by inhibiting peptide bond formation during translation.

22. A method according to claim 21 wherein a sequence derived from the sequence of FMDV 2A mediates said automatic cleavage.

23. A method according to claim 21 wherein said second portion includes the sequence of FMDV 2A modified to increase or decrease the efficiency of automatic cleavage.

24. A particle-forming moiety produced by the method according to claim 1.

25. A method of producing a particle-forming moiety, said method comprising:
 a) providing a first virus or pseudovirus containing a polynucleotide encoding a chimeric protein having a first, viral coat protein, portion and a second, foreign peptide or protein, portion, wherein said second portion consists of over 25 amino acids and includes a sequence able to mediate automatic cleavage of a proportion of the chimeric protein expressed at a predetermined site therein to yield a particle-forming moiety and a target moiety, wherein said particle-forming moiety and any uncleaved chimeric protein are capable of co-assembly into a rod-shaped product virus or pseudovirus such that any second portion is disposed on the exterior surface of the assembled product virus or pseudovirus;
 b) infecting a host cell with the first virus or pseudovirus; and
 c) allowing replication and expression of the polynucleotide in the host cell to produce said particle-forming moiety and said target moiety.

26. A method according to claim 25 including the step of allowing self-assembly of said particle-forming moiety and any uncleaved chimeric protein together with a copy of said polynucleotide to form a product virus or pseudovirus capable of replicating and assembling in plants.

27. A method according to claim 26, including the step of purifying the product virus or pseudovirus from the host cell.

28. A method according to claim 27, including the step of cleaving at least a part of the second portion from the product virus or pseudovirus after purification of the product virus or pseudovirus from the host cell.

29. A method according to claim 25 wherein substantially all of said chimeric protein undergoes automatic cleavage to yield said particle-forming moiety and said target moiety, and wherein said particle-forming moiety alone with said polynucleotide is capable of assembly into a rod-shaped product virus or pseudovirus such that any second portion is disposed on the exterior of the assembled product virus or pseudovirus.

30. A product virus or pseudovirus provided by the method according to claim 26 or 29.

31. A method according to claim 29, including the step of purifying protein derived from the second portion from the host cell after replication and expression of the polynucleotide in the host cell.

32. A method according to claim 25, wherein a linker peptide is incorporated between the first and second portions.

33. A method according to claim 25, including the step of purifying target moiety from the host cell.

34. A method according to claim 25, wherein the product virus or pseudovirus is a plant virus or a pseudovirus thereof.

35. The method according to claim 34, wherein the product virus or pseudovirus is selected from the group consisting of potexvirus, polyvirus and pseudoviruses thereof.

36. A method according to claim 35, wherein the product virus or pseudovirus is potato virus X or a pseudovirus thereof.

37. A method according to claim 25, wherein the second portion is located at or adjacent to the N-terminus of the first portion.

38. A method according to claim 25, wherein the second portion is selected from the group consisting of a proteinaceous diagnostic reagent, an antibiotic, a therapeutic agent, a pharmaceutically active agent, an antigenic epitope and a food supplement.

39. A method according to claim 25, wherein the product virus or pseudovirus comprises a mixture of particle-forming moiety and wild-type coat protein.

40. A method according to claim 25, wherein the product virus or pseudovirus has a pitch of helix of more than 2 nm.

41. A method according to claim 25, wherein the product virus or pseudovirus is flexuous.

42. A method according to claim 25, wherein in step b) the host cell is infected with a first virus or pseudovirus particle which is a plant virus or a pseudovirus.

43. A method according to claim 25, wherein in step b) the host cell is infected with a first virus or pseudovirus which is modified potato virus X or a pseudovirus thereof.

44. The method according to claim 25 wherein the second portion has over 30 amino acids.

45. The method according to claim 25, wherein the second portion or a peptide derived therefrom has a molecular weight in excess of 10 kDa.

46. The method according to claim 25 wherein said automatic cleavage occurs by inhibiting of peptide bond formation during translation.

47. The method according to claim 45 wherein a sequence derived from the sequence of FMDV 2A mediates said automatic cleavage.

48. The method according to claim 45 wherein said second portion includes the sequence of FMDV 2A modified to increase or decrease the efficiency of automatic cleavage.

49. A particle-forming moiety produced by the method according to claim 25.

* * * * *

UNITED STATES PATENT AND TRADEMARK OFFICE
CERTIFICATE OF CORRECTION

PATENT NO. : 6,232,099 B1
DATED : May 15, 2001
INVENTOR(S) : Chapman et al.

It is certified that error appears in the above-identified patent and that said Letters Patent is hereby corrected as shown below:

Column 28,
Line 52, should read:
47. The method according to claim 46 wherein a sequence
Line 55, should read:
48. The method according to claim 46 wherein said Signed and Sealed this Fifth Day of March, 2002

Attest:

JAMES E. ROGAN
*Attesting Officer*     *Director of the United States Patent and Trademark Office*